(12) United States Patent
Omori et al.

(10) Patent No.: US 8,721,617 B2
(45) Date of Patent: May 13, 2014

(54) LIQUID COMPONENT COLLECTING DEVICE

(75) Inventors: Masayoshi Omori, Hiroshima (JP);
Seishin Tanaka, Hiroshima (JP);
Yasunori Okamoto, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 13/147,300

(22) PCT Filed: Jan. 22, 2010

(86) PCT No.: PCT/JP2010/000357
§ 371 (c)(1),
(2), (4) Date: Aug. 26, 2011

(87) PCT Pub. No.: WO2010/089965
PCT Pub. Date: Aug. 12, 2010

(65) Prior Publication Data
US 2011/0301564 A1     Dec. 8, 2011

(30) Foreign Application Priority Data

Feb. 4, 2009   (JP) ................................. 2009-024300

(51) Int. Cl.
*B01D 21/26*     (2006.01)
(52) U.S. Cl.
USPC ............................ 604/416; 210/787; 604/408
(58) Field of Classification Search
USPC ........................................................ 604/416
See application file for complete search history.

(56) References Cited

U.S. PATENT DOCUMENTS

| 4,344,560 A | 8/1982 | Iriguchi et al. |
| 4,447,220 A | 5/1984 | Eberle |

(Continued)

FOREIGN PATENT DOCUMENTS

| CN | 2246514 | 2/1997 |
| CN | 2274956 | 2/1998 |

(Continued)

OTHER PUBLICATIONS

Office Action for U.S. Appl. No. 12/670,971, mailed Aug. 17, 2012.

(Continued)

*Primary Examiner* — Leslie Deak
*Assistant Examiner* — Sara Sass
(74) *Attorney, Agent, or Firm* — Pearl Cohen Zedek Latzer Baratz LLP

(57) ABSTRACT

A liquid component collecting device capable of more easily collecting a liquid component. A liquid component collecting device (100) is provided with: a flexible cylindrical liquid component storage container (21) having an opening at one end thereof; a cylindrical first housing container (22) for housing the liquid component storage container (21) and having an opening at one end thereof; and a first cap (23) connected to the opening in the liquid component storage container (21) and fitted to the opening in the first housing container (22). A pressure regulating space (26) independent of the internal space of the liquid component storage container (21) is formed between the outer side of the liquid component storage container (21) and the inner side of the first housing container (22). The first cap (23) is provided with a liquid component inlet channel (27) for introducing blood into the liquid component storage container (21), a first communication channel (28) communicating with the internal space of the liquid component storage container (21), and a second communication channel (29) communicating with the pressure regulating space (26).

9 Claims, 15 Drawing Sheets

(56) References Cited

U.S. PATENT DOCUMENTS

| | | | |
|---|---|---|---|
| 4,516,973 A | 5/1985 | Telang | |
| 4,573,992 A | 3/1986 | Marx | |
| 4,917,804 A | 4/1990 | Franks et al. | |
| 5,224,921 A | 7/1993 | Dennehey et al. | |
| 5,275,585 A | 1/1994 | Olson | |
| 5,632,906 A * | 5/1997 | Ishida et al. | 210/787 |
| 6,325,750 B1 | 12/2001 | Jorgensen et al. | |
| 6,686,204 B2 * | 2/2004 | Dubrowny et al. | 436/69 |
| 7,249,618 B2 * | 7/2007 | Lacroix | 141/313 |
| 8,419,705 B2 | 4/2013 | Omori et al. | |
| 2006/0113228 A1 * | 6/2006 | Rosiello | 210/143 |
| 2006/0251622 A1 | 11/2006 | Suzuki et al. | |
| 2010/0211041 A1 * | 8/2010 | Omori et al. | 604/403 |

FOREIGN PATENT DOCUMENTS

| | | |
|---|---|---|
| CN | 1791438 | 6/2006 |
| GB | 1569219 | 6/1980 |
| JP | S57-49461 | 3/1982 |
| JP | 58-209358 | 12/1983 |
| JP | H02-501356 | 5/1990 |
| JP | H04-27943 | 3/1992 |
| JP | H05-500624 | 2/1993 |
| JP | H06-14992 | 1/1994 |
| JP | 2002-538900 | 11/2002 |
| JP | 2003-19184 | 1/2003 |
| JP | 2003-93517 | 4/2003 |
| JP | 3788479 | 6/2006 |
| JP | 2007-259898 | 10/2007 |
| JP | 2008-311150 | 12/2008 |
| WO | WO 88/10124 | 12/1988 |
| WO | WO 2006/079237 | 8/2006 |

OTHER PUBLICATIONS

Office Action Issued for U.S. Appl. No. 12/670,971, mailed on Aug. 17, 2012.

* cited by examiner

US 8,721,617 B2

LIQUID COMPONENT COLLECTING DEVICE

CROSS-REFERENCE TO RELATED APPLICATIONS

This application is a National Phase Application of PCT International Application No. PCT/JP2010/000357, International Filing Date Jan. 22, 2010, claiming priority of Japanese Patent Application, JP 2009-024300, filed Feb. 4, 2009, which is entirely incorporated herein by reference.

TECHNICAL FIELD

The present invention relates to a liquid component collecting device for collecting a liquid component such as blood or urine.

BACKGROUND ART

Currently, in the field of regenerative medicine, studies are being carried out in which stem cells collected from a subject are caused to proliferate or differentiate ex vivo, and are thereafter transplanted into a subject, thereby promoting regeneration of tissue of the subject. Stem cells are multipotent and can differentiate into a variety of tissues and organs, and they have been attracting attention as cells which are the key to regenerative medicine.

It has been known that the addition of a serum to the medium is effective in ex vivo cultural proliferation of stem cells. However, when an objective relates to human therapies, the use of a serum derived from an animal other than humans should be avoided in light of possible safety problems. Therefore, there is a demand for the use of a serum prepared from blood collected from a human, and in particular, collected from the same subject. Furthermore, in comparison to a blood test, cultivation of stem cells in the field of regenerative medicine requires a relatively large amount of serum. In addition, in order to prepare serum assuming application to a human, it is required to separate and store the serum aseptically in a closed system.

As a response to the abovementioned various requirements, the present applicants have already disclosed a serum preparation apparatus including: a blood storage part for storing blood, and a component storage part linked aseptically and in an air-tight manner to the blood storage part, the blood storage part having a blood coagulation promotion substance that is in contact with the blood and promotes coagulation, and the blood coagulation promotion substance producing serum aseptically (refer to Patent Document 1).
Patent Document 1: Japanese Patent No. 3788479

SUMMARY OF THE INVENTION

Problems to be Solved by the Invention

The serum preparation apparatus described in Cited Reference 1 can produce serum quickly and efficiently while ensuring a high level of safety. In the serum preparation apparatus described in Patent Document 1, blood is collected by inserting into a subject a puncturing needle attached to one end of a blood drawing tube, the other end being connected to a blood component preparation container that is a blood storage part. When the blood that has been collected is introduced into the blood component preparation container, the subject's blood pressure, and the drop in pressure between the position at which blood is drawn from the subject (the position at which the puncturing needle used for taking blood is inserted) and an installation position of the blood component preparation container.

However, in a case where the blood pressure of the subject is low, a prescribed amount of blood cannot be collected using the blood pressure, and in a case where a relatively small amount of blood is collected, it has been difficult to have a sufficient pressure drop between the position at which blood is drawn from the subject and the installation position of the blood component preparation container.

Furthermore, besides blood, liquid components such as urine and the like may be collected from the subject, but in this case also, it has been difficult to have a sufficient pressure drop between the position at which blood is drawn from the subject and the installation position of the container for collecting the liquid component.

Consequently, it is an object of the present invention to provide a liquid component collecting device, in which it is possible to easily take a liquid component, without depending on the subject's blood pressure or the pressure drop between the position at which blood is taken from the subject and the installation position of the blood component preparation container.

Means for Solving the Problems

The present invention provides a liquid component collecting device that includes: a flexible cylindrical liquid component storage container having an opening at one end; a cylindrical first housing container for housing the liquid component storage container and having an opening at one end; and a first cap connected to the opening in the liquid component storage container and fitted to the opening in the first housing container; wherein a pressure regulating space, which is a space that is independent of an internal space of the liquid component storage container, is formed between an outer side of the liquid component storage container and an inner side of the first housing container; and a liquid component inlet channel for introducing a liquid component to the liquid component storage container, a first communication channel communicating with an internal space of the liquid component storage container, and a second communication channel communicating with the pressure regulating space, are provided in the first cap, to realize the abovementioned object.

Effects of the Invention

According to the liquid component collecting device of the present invention, it is possible to more easily collect a liquid component such as blood, urine, or the like.

EXPLANATION OF REFERENCE NUMERALS

Figure 1:
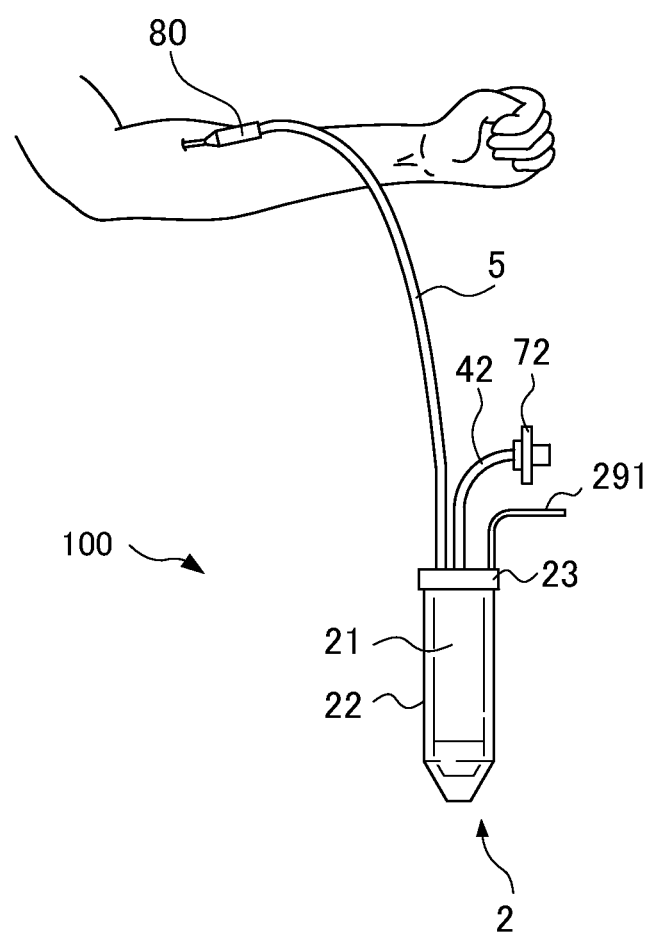
FIG. 1 is a drawing showing a first embodiment of a blood collecting device according to one embodiment of a liquid component collecting device of the present invention.

1 blood component separation and storage apparatus
2 blood storage part
21 blood storage container (liquid component storage container)
22 first housing container
23 first cap
24 first connecting part
25 second connecting part
26 pressure regulating space
27 blood inlet channel (fluid inlet channel, liquid component inlet channel)
28 first communication channel (component outlet channel)
29 second communication channel (injection hole)
3 component storage part
31 component storage container
32 second housing container
33 second cap
341 component collection orifice
35 third connection part
36 fourth connection part
37 component inlet channel
38 ventilation channel
4 linking part
41 linking tube
42 ventilation tube
5 blood drawing tube
6 blood coagulation promotion substance
7 ventilation tube
71, 72 ventilation filter
80 blood drawing needle
100, 100A, 100B blood collecting device (liquid component collecting device)

DETAILED DESCRIPTION OF THE INVENTION

The present invention is described below based on preferable embodiments thereof, making reference to the drawings.

Figure 2:
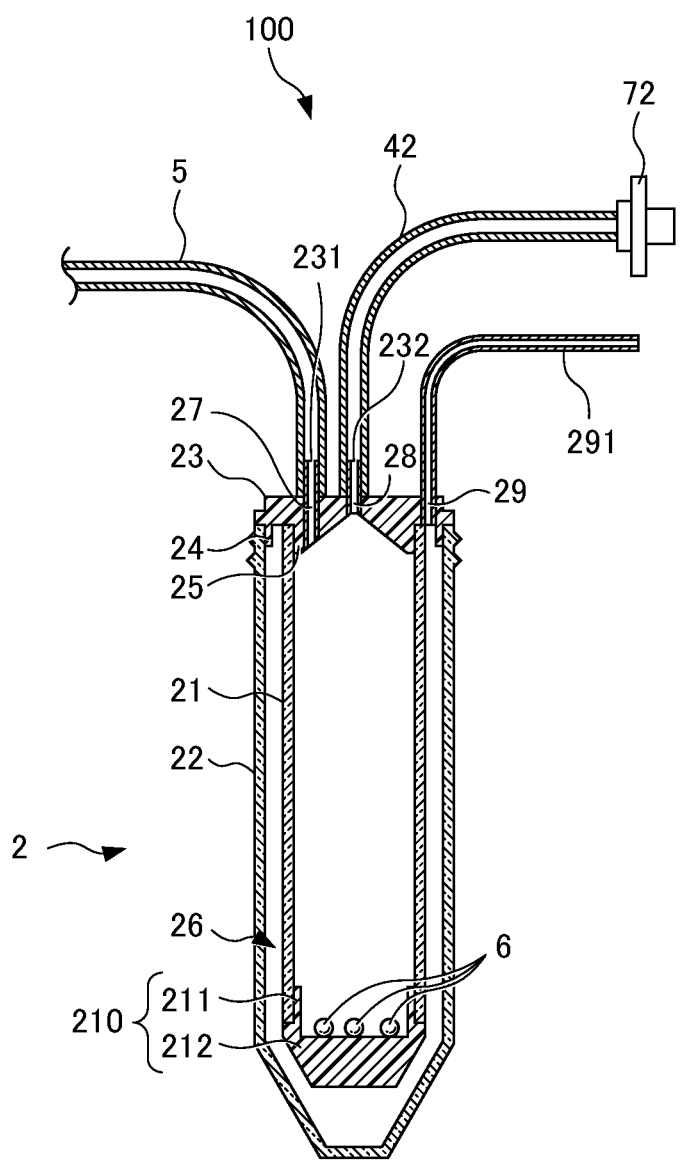
FIG. 2 is a partially expanded view of FIG. 1.
Figure 3:
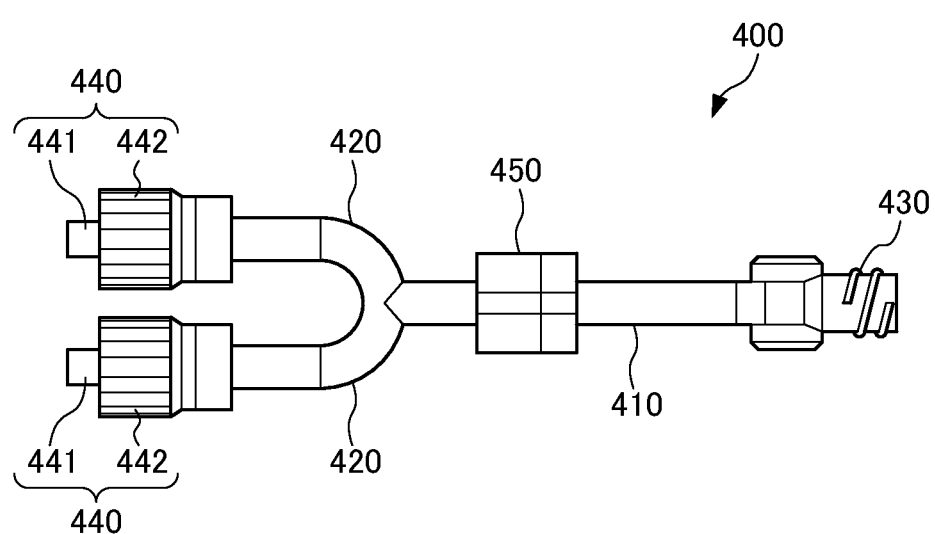
FIG. 3 is a drawing showing a pressure regulation support device preferably used in the liquid component collecting device of the present invention.

First, a description is given concerning a first embodiment of a blood collecting device 100 according to a preferable embodiment of a liquid component collecting device of the present invention, making reference to FIG. 1 to FIG. 3.

FIG. 1 is a drawing showing a state in which blood is collected by the blood collecting device 100. FIG. 2 is a partially expanded view of FIG. 1. FIG. 3 is a drawing showing a pressure regulation support device 400 preferably used in the blood collecting device 100.

The blood collecting device 100 of the first embodiment is preferably used in a case of collecting a relatively small amount of blood. It is to be noted that the liquid component collecting device of the present invention is not limited to cases of collecting blood, and is preferably used in cases of collecting various types of liquid components that are required to be collected aseptically, such as various types of body fluid including urine or drainage of peritoneal dialysis fluid, various types of cell components such as adipocytes, and cultured cell suspensions.

The blood collecting device 100, as shown in FIG. 1 and FIG. 2, is provided with a blood storage container 21 as a liquid component storage container, a first housing container 22 for housing the blood storage container 21, and a first cap 23 connected to the blood storage container 21 and the first housing container 22.

The blood storage container 21, as shown in FIG. 2, has a longitudinal cylindrical shape, and is formed from a material whose side face is flexible. Furthermore, a cross section in a radial direction of the blood storage container 21 has an elliptical shape.

A side face of the blood storage container 21 is preferably composed of material that is transparent from a viewpoint in which blood stored inside the blood storage container 21 is visible. For the flexible material it is possible to use polyvinyl chloride, polyethylene, polypropylene, polyurethane, silicone, ethylene-vinyl acetate copolymer resin, synthetic rubber, and soft synthetic resin such as various types of elastomer. An upper end which is one end of the blood storage container 21 has an opening, and is hermetically sealed by fitting the first cap 23. A bottom cap 210 is fitted to a lower end portion which is the other end of the blood storage container 21, and is joined by an adhesive.

The bottom cap 210 is provided with a cylindrical fitting part 211 and a bottom part 212 contiguous with the fitting part 211. A cross section in a radial direction of the fitting part 211 has an elliptical shape, and an external diameter thereof is approximately the same as an internal diameter of the blood storage container 21. With regard to the bottom cap 210, the fitting part 211 fits a lower end portion of the blood storage container 21. The diameter of the bottom part 212 gradually decreases in a downward direction, after which a bottom face thereof has a flat shape.

The first housing container 22, as shown in FIG. 2, has a longitudinal cylindrical shape similar to the blood storage container 21, and is configured such that its diameter and height are both slightly larger than the blood storage container 21. An upper end, which is one end of the first housing container 22, also has an opening, and can be hermetically sealed by fitting the first cap 23. In a vicinity of a lower end, which is the other end of the first housing container 22, the diameter of the first housing container 22 gradually decreases in a downward direction, after which it has an upper-lower reversed conical shape with a flat bottom face on the head thereof.

The first housing container 22 preferably is formed from material that is transparent from a viewpoint in which fluid stored inside the blood storage container 21 is visible, and is preferably formed from material having relatively large rigidity. With regard to the material of which the first housing container 22 is composed, specifically, polycarbonate, polyethylene, polypropylene, polyester, polymethylpentene, methacryl, ABS resin (acrylonitrile butadiene styrene copolymer), PET resin (polyethylene-telephthalate), and polyvinyl chloride may be cited. The hard synthetic resin refers to synthetic resin having hardness of an extent that does not easily deform due to a pressure variation of an internal space of a container due to injection of fluid to be described later.

A screw ridge is formed on an outer side face in a vicinity of the upper end of the first housing container 22, and a cover cap (not shown in the drawings) having a screw trough corresponding to the screw ridge can be screwed on. By screwing the cover cap onto the first housing container 22, it is possible to prevent the first cap 23 from coming off the first housing container 22 during a blood collecting operation, as described later.

The first cap 23 has a flat face with a circular shape, and its diameter is approximately the same as the outer diameter of the first housing container 22 (refer to FIG. 2). The first cap 23, on a lower face that is one face thereof, has a first connecting part 24 that can be connected to the first housing container 22, and a second connecting part 25 that can be connected to the blood storage container 21 on an inner side of the first connecting part 24. The first connecting part 24 and the second connecting part 25 have forms that protrude in a downward direction.

An outer diameter of the first connecting part 24 is approximately the same as an inner diameter of the opening of the first housing container 22, and a vicinity of the opening of the first housing container 22 can be fitted to an outer peripheral face of the first connecting part 24. An outer diameter of the second connecting part 25 is approximately the same as an inner diameter of the opening of the blood storage container 21, and a vicinity of the opening of the blood storage container 21 can be fitted to an outer peripheral face of the second connecting part 25.

That is, in the present embodiment, the blood storage container 21 and the first housing container 22 that houses the blood storage container 21 are both configured to be fitted to the first cap 23. The first housing container 22 is hermetically sealed by being fitted to the first cap 23. Furthermore, in this way, a pressure regulating space 26, which is a space independent of an internal space of the blood storage container 21, is formed between an outer side of the blood storage container 21 and an inner side of the first housing container 22.

A hermetically sealing member (not shown in the drawings) for improving sealing of the pressure regulating space 26 is interposed between the outer peripheral face of the first connecting part 24 and an inner peripheral face in the vicinity of the opening of the first housing container 22. In this way, it is possible to ensure a hermetically sealed structure with more certainty for the pressure regulating space 26.

As a hermetically sealing member, it is possible to use, for example, a ring shaped member formed from silicon rubber. The hermetically sealing member may have a configuration which can cap the outer peripheral face of the first connecting part 24; material is not limited to the abovementioned silicon rubber, and it is possible to use an elastic member such as various types of rubber, various types of elastomer, and the like.

Furthermore, the hermetically sealing member may be disposed between an outer peripheral face of the second connecting part 25 and an inner peripheral face in the vicinity of the opening of the blood storage container 21.

The first cap 23 is provided with a blood inlet channel 27 for introducing blood into the blood storage container 21, a first communication channel 28 communicating with an internal space of the blood storage container 21, and a second communication channel 29 communicating with the pressure regulating space 26. In the first embodiment, a fluid inlet channel 27 and a component outlet channel 28 are provided in the first cap 23, as shown in FIG. 2. The blood inlet channel 27 and the first communication channel 28 are arranged by forming a through hole penetrating the first cap 23 from an upper face thereof to a lower face.

The shape of a portion facing the internal space of the blood storage container 21, in the lower face of the first cap 23, as shown in FIG. 2, is preferably formed to have a gradually decreasing diameter in an upward direction. In addition, a preferable configuration is one in which the first communication channel 28, which is a through hole in a top part thereof, is provided. With the abovementioned configuration it is possible to prevent blood stored inside the blood storage container 21 from mistakenly flowing out from the first communication channel 28.

A blood drawing tube 5 is connected to the blood inlet channel 27, and blood drawn from a subject passes through the blood drawing tube 5 and the blood inlet channel 27, to be stored aseptically in the blood storage container 21. The blood inlet channel 27 and the blood drawing tube 5 are connected by engaging an end part of the blood drawing tube 5 with a first protruding part 231 arranged on an upper face of a portion in which the blood inlet channel 27 is formed, in the first cap 23.

A ventilation tube 42 is connected to the first communication channel 28, and a ventilation filter 72 is connected to an extremity side of the ventilation tube 42. The ventilation filter 72 is a filter having properties such that gas can pass but fluid cannot pass, and furthermore microbes also cannot pass. That is, it is possible for air to ascetically enter or exit the inside of the blood storage container 21 from the first communication channel 28 to which the ventilation filter 72 is attached.

The first communication channel 28 and the ventilation tube 42 are connected by engaging an end part of the ventilation tube 42 to a second protruding part 232 arranged on an upper face in a portion in which the first communication channel 28 is formed, in the first cap 23.

The second communication channel 29 is formed in an area on an outer side of the second connecting part 25 and an inner side of the first connecting part 24 in the first cap 23. One end of a fluid injection tube 291 is connected to the second communication channel 29, and an injection unit (not shown in the drawings), which can inject fluid to the inside of the pressure regulating space 26, is connected to the other end of the fluid injection tube 291. A pump, a syringe, or the like can be used as the injection unit.

By injecting fluid from the second communication channel 29 by the injection unit, the pressure regulating space 26 is pressurized. At this time, since the first housing container 22 forming an outer side of the pressure regulating space 26 is not flexible, the blood storage container 21, which is flexible, is affected by the pressurization of the pressure regulating space 26 and is deformed as if being crushed. Furthermore, the blood storage container 21 that is deformed as if being crushed by the pressurization of the pressure regulating space 26 is restored to its original shape by depressurizing the pressure regulating space 26 that has been pressurized. In this way, by deforming the blood storage container 21 by pressurizing and depressurizing the pressure regulating space 26, it is possible to easily and aseptically draw blood.

The fluid that is injected into the pressure regulating space 26 may be a gas such as air, or may be a fluid such as water. Furthermore, a gel form may be used as the fluid. The above is preferable in the point that, in a case of using a fluid such as water or a substance in a gel form as the fluid, since the volume of the fluid does not change due to added pressure at time of injection, it is possible to accurately comprehend the amount of serum and the like that is extracted to a component storage part 3.

In the blood collecting device 100 above, blood collecting is performed in a first procedure or a second procedure as follows.

In the first procedure, first, air is injected into the pressure regulating space 26 from the second communication channel 29, and the pressure regulating space 26 is pressurized. In this way, the blood storage container 21 is deformed as if being crushed.

In this state, a blood drawing needle 80 is inserted into the subject (patient). Next, the air of the internal space of the blood storage container 21 is drawn from the ventilation tube 42 that is connected to the first communication channel 28, and the air of the pressure regulating space 26 is drawn from the fluid injection tube 291 that is connected to the second communication channel 29. Thereupon, by the air of the internal space of the blood storage container 21 being drawn and a pressurized state of the pressure regulating space 26 being released, so that the blood storage container 21 is restored to its original form, a negative pressure is applied inside the blood storage container 21. In this way, blood collected by the blood drawing needle 80 is introduced into the blood storage container 21 by being strongly drawn to the blood storage container 21 side.

Next, a description is given concerning the second procedure. In the second procedure, first, a path of the blood drawing tube 5 is closed by a clamp (not shown in the drawings) or the like. Next, the air of the internal space of the blood storage container 21 is drawn from the ventilation tube 42 that is connected to the first communication channel 28, and the air of the pressure regulating space 26 is drawn from the fluid injection tube 291 that is connected to the second communication channel 29. Thereupon, a negative pressure is applied to the internal space of the blood storage container 21 and the pressure regulating space 26. In this case, since a pressure difference does not occur between the internal space of the blood storage container 21 and the pressure regulating space 26, even if a negative pressure is applied to the internal space of the blood storage container 21, the blood storage container 21 does not deform (is not crushed).

In this state, after the blood drawing needle 80 has been inserted in the subject (patient), the path of the blood drawing tube 5 is opened. Thereupon, the blood drawn by the blood drawing needle 80 is strongly drawn to the blood storage container 21 by the negative pressure of the internal space of the blood storage container 21, and is introduced to the blood storage container 21.

According to the second procedure, in a process of drawing blood, deformation of the blood storage container 21 does not occur. Therefore, since the blood storage container 21 is not crushed when drawing of blood is performed, in a case where a scale showing the amount of blood drawn is attached to the blood storage container 21, it is possible to accurately comprehend the amount of blood drawn.

According to the blood drawing device 100 of the present embodiment as above, blood is easily drawn without depending on the blood pressure of the subject or a pressure drop between the position at which blood is taken from the subject and an installation position of the blood drawing device.

It is to be noted that in a case where air is drawn at the same time from two places: the ventilation tube 42 and the fluid injection tube 291, it is preferable to use a pressure regulation support device 400, as shown in FIG. 3. The pressure regulation support device 400 is provided with a first air flow channel 410, a pair of second air flow channels 420 arranged at one end of the first air flow channel 410 and with an extremity split into 2, a first connection part 430 arranged at the other end of the first air flow channel 410, a pair of second connection parts 440 arranged at respective extremities of the pair of second air flow channels 420, and a unidirectional valve 450 arranged in the first air flow channel 410.

The first air flow channel 410 and the pair of second air flow channels 420 are formed by tubes that are flexible.

The first connection part 430 is formed from a hard synthetic resin, and is linked to an extremity of the first air flow channel 410. An air drawing device such as a syringe (not shown in the drawings) is connected to the first connection part 430.

The pair of second connection parts 440 is formed from a hard synthetic resin, and is linked to an extremity of the pair of second air flow channels 420. The second connection parts 440 are provided with a connection part main unit 441, and a nut member 442 disposed on an outer side of the connection part main unit 441. One among the pair of second connection parts 440 is connected to the ventilation tube 42, and the other among the pair of second connection parts 440 is connected to the fluid injection tube 291. Connections between the pair of second connection parts 440, and the ventilation tube 42 and the fluid injection tube 291 are fixed by the nut member 442.

The unidirectional valve 450 is configured by a valve unit that allows flow of a fluid (air) only from the pair of second connection parts 440 to the first connection part 430 side.

According to the pressure regulation support device 400 as above, in a state where the pair of second connection parts 440 is connected to the ventilation tube 42 and the fluid injection tube 491, the air drawing device is connected to the first connection part 430, and by drawing the air by this air drawing device, the air of the internal space of the blood storage container 21 and the air of the pressure regulating space 26 is drawn at the same time, via the ventilation tube 42 and the flow injection tube 291, and both the internal space of the blood storage container 21 and the pressure regulating space 26 can both be depressurized to the same extent at the same time.

Furthermore, since the unidirectional valve 450, that allows flow of a fluid (air) only from the pair of second connection parts 440 to the first connection part 430 side, is disposed in the first air flow channel 410, air does not enter from the first connection part 430 side to the pair of second connection parts 440. Therefore, by disposing the unidirectional valve 450 in the first air flow channel 410, it is possible to maintain a depressurized state of the internal space of the blood storage container 21 and the pressure regulating space 26. In addition it is possible to ensure sterility of internal space of the blood storage container 21.

The following effect is realized by the blood collecting device 100 of the first embodiment as described above.

The blood collecting device 100 is configured to include a flexible blood storage container 21, a first housing container 22 made of hard synthetic resin for housing the blood storage container 21, and a pressure regulating space 26 formed between the blood storage container 21 and the first housing container 22. In this way, by pressurizing and depressurizing the pressure regulating space 26, it is possible to easily and aseptically draw blood. Therefore, blood is easily drawn without depending on the blood pressure of the subject or a pressure drop between the position at which blood is taken from the subject and an installation position of the blood drawing device.

Furthermore, the ventilation tube 42 provided with the ventilation filter 72 is linked to the first communication channel 28. In this way, air can be aseptically taken in and out of the blood storage container 21. Thus, by drawing air of the internal space of the blood storage container 21 from the ventilation tube 42, collecting of blood can be carried out more smoothly.

Furthermore, the cross section in a radial direction of the blood storage container 21 is formed in an elliptical shape. In this way, in a case of pressurizing the pressure regulating space 26, since the blood storage container 21 is easily deformed, drawing of blood by the blood collecting device 100 can be carried out more easily.

Figure 4:
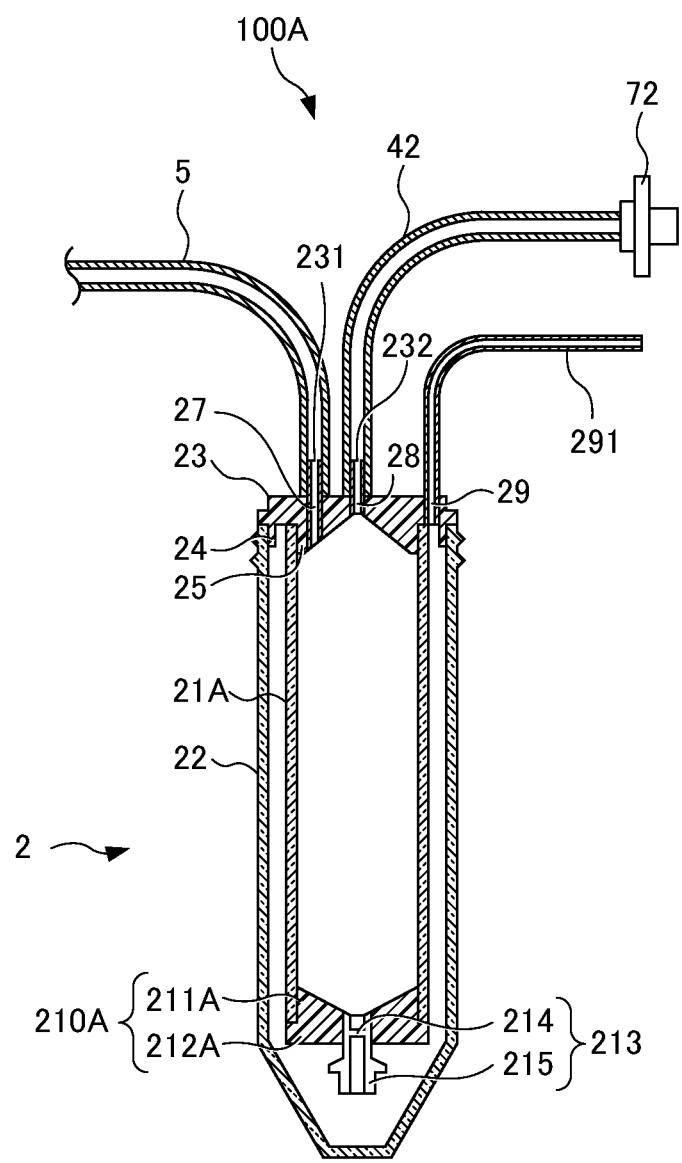
FIG. 4 is a drawing showing a second embodiment of the blood collecting device.

Next, a description is given concerning a second embodiment of the liquid component collecting device of the present invention, making reference to FIG. 4. FIG. 4 is a drawing showing a blood collecting device 100A of the second embodiment.

It is to be noted that in the description of the second embodiment and following, the same component elements are given the same reference symbols, and descriptions thereof are omitted or simplified.

The blood collecting device 100A of the second embodiment differs from the first embodiment with regard to a blood storage container 21A. More specifically, there is a difference from the first embodiment in the point that there is provided a first liquid component collecting part 213 for collecting liquid components contained in the blood storage container 21A at a lower end of the blood storage container 21A. The first liquid component collecting part 213 is provided with a first liquid component collection orifice 214 formed in a bottom part 212A of a bottom cap 210A, and a hollow cylindrical part 215 arranged at a lower portion of the first liquid component collection orifice 214.

The first liquid component collection orifice 214 is formed by providing a thin area of a thin film form in part of the bottom part 212A of the bottom cap 210A. The cylindrical part 215 protrudes downwards from the bottom of the bottom part 212A, in an area formed at the first liquid component collection orifice 214.

Blood components contained in the blood storage container 21A can be collected by breaking and puncturing the first liquid component collection orifice 214 with a puncturing tool such as a syringe needle or the like. At this time, since the hollow cylindrical part 215 is formed in an area in which the first liquid component collection orifice 214 is formed, it is possible to assuredly puncture the component collection orifice 214 with the puncturing tool.

It is to be noted that as shown in FIG. 4, the shape of the bottom part 212A of the bottom cap 210A is preferably formed to have a gradually decreasing diameter in a downward direction. In addition, the first liquid component collection orifice 214 is preferably arranged at an apex thereof. With the abovementioned configuration, when blood components are collected inside the blood storage container 21A, it is possible to collect the blood components without waste Furthermore, distance between the position of the first liquid component collection orifice 214 and the position of an inner bottom part of the first housing container 22 is preferably set to a distance whereby the puncturing tool can be housed.

With the abovementioned configuration, it is possible to house the puncturing tool within the first housing container 22 in a state puncturing the first liquid component collection orifice 214. If the puncturing tool has an open-close structure, collection and storage of the blood components inside the component storage container 21A is possible in accordance with requirements.

According to the blood collecting device 100A of the second embodiment, besides realizing an effect similar to the first embodiment, an effect as below is realized.

The first liquid component collecting part 213 is provided at a bottom end of the blood storage container 21A. In this way, it is possible to collect blood components aseptically from the bottom end of the blood storage container 21A. Therefore, a precipitation component such as blood cell components, among blood components stored in the blood storage container 21A, can be collected easily and aseptically without mixing other components.

Furthermore, in a case of applying the present embodiment to a collecting device for cell suspensions, as a liquid component collecting device, it is possible to easily and aseptically collect cells as precipitation components, without mixing other components.

Figure 5:
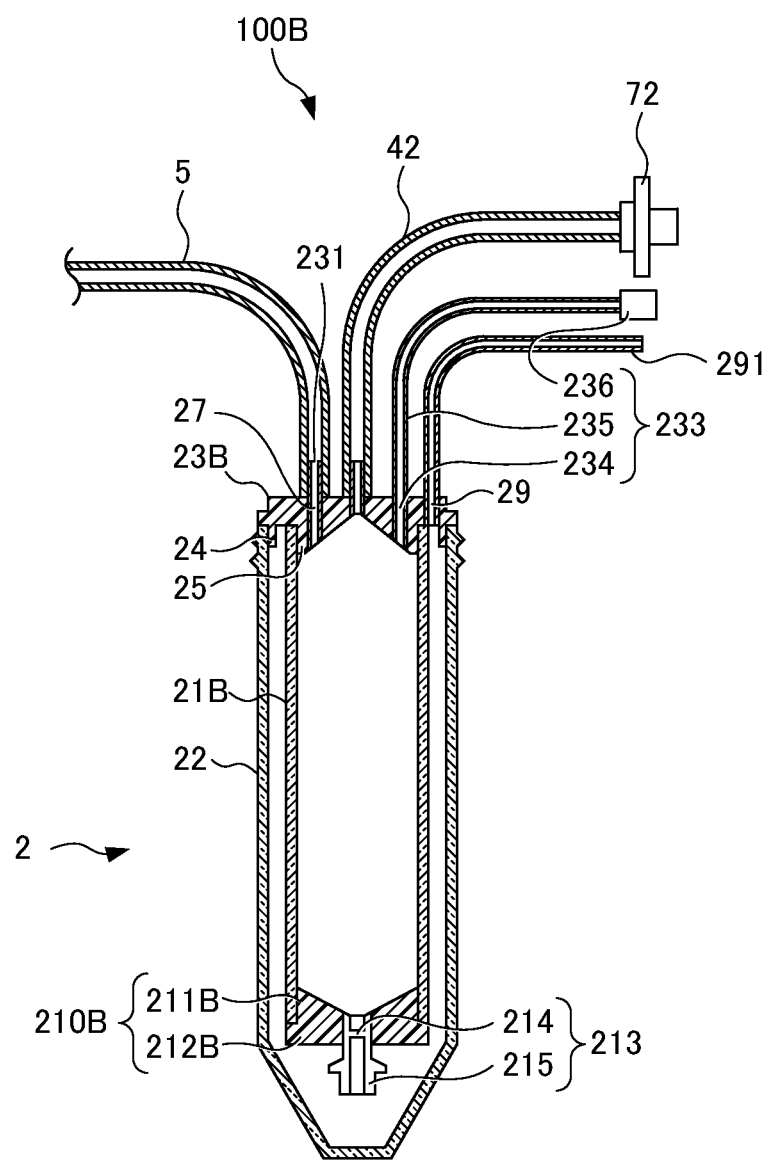
FIG. 5 is a drawing showing a third embodiment of the blood collecting device.

Next, a description is given concerning a third embodiment of the liquid component collecting device of the present invention, making reference to FIG. 5. FIG. 5 is a drawing showing a blood collecting device 100B of the third embodiment.

The blood collecting device 100B of the third embodiment differs from the second embodiment in the point that a second liquid component collecting unit 233 is provided at an upper end of a blood storage container 21B. More specifically, the second liquid component collecting unit 233 is provided with a liquid component collecting channel 234 arranged in a first cap 23B, a liquid component collecting tube 235 connected to the liquid component collecting channel 234, and a connection part 236 that can connect to a liquid component collecting device (not shown in the drawings) such as a syringe or the like, being connected to an extremity side of the liquid component collecting tube 235.

The connection point 236 is connected by being fitted or screwed to the liquid component collecting tube 235. A co-injecting port provided with a valve unit having a slit into which an extremity of a syringe can be inserted and removed, for example, can be preferably used as the connecting part 236.

According to the blood collecting device 100B of the third embodiment, besides realizing an effect similar to the second embodiment, an effect is realized as follows.

The second liquid component collecting unit 233 is provided at an upper end of the blood storage container 21B. In this way, blood components are collected aseptically from the upper end of the blood storage container 21B. Therefore, a supernatant component such as plasma, serum, or the like, among blood components stored in the blood storage container 21B can be easily and aseptically collected, without mixing with other components.

It is to be noted that in the third embodiment, the first liquid component collecting unit 213 and the second liquid component collecting unit 233 are provided in the blood storage container 21B, but there is no limitation to this. That is, the second liquid component collecting unit only may be provided in the blood storage container.

Next, a description is given concerning various preferable embodiments of the blood component separation and storage apparatus 1 that uses the blood collecting device 100 according to the first embodiment of the liquid component collecting device of the present invention.

Figure 6:
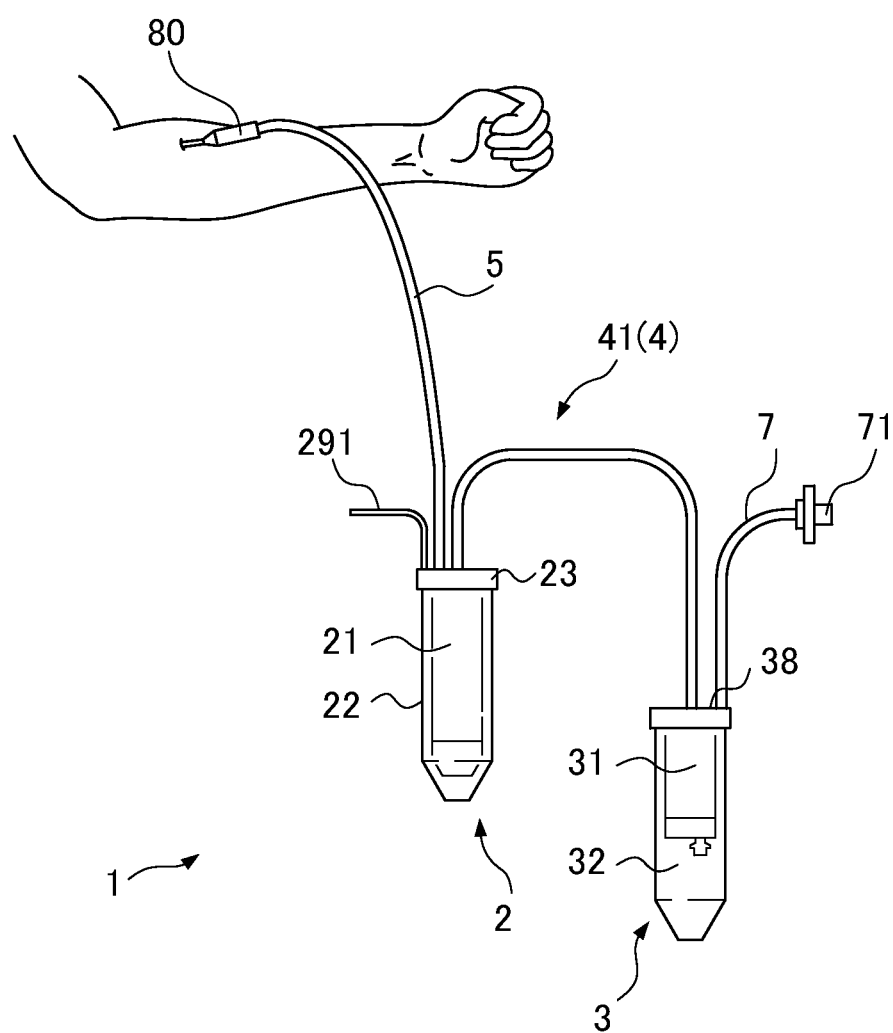
FIG. 6 is a drawing showing the first embodiment of a blood component separation and storage apparatus of the present invention.
Figure 7:
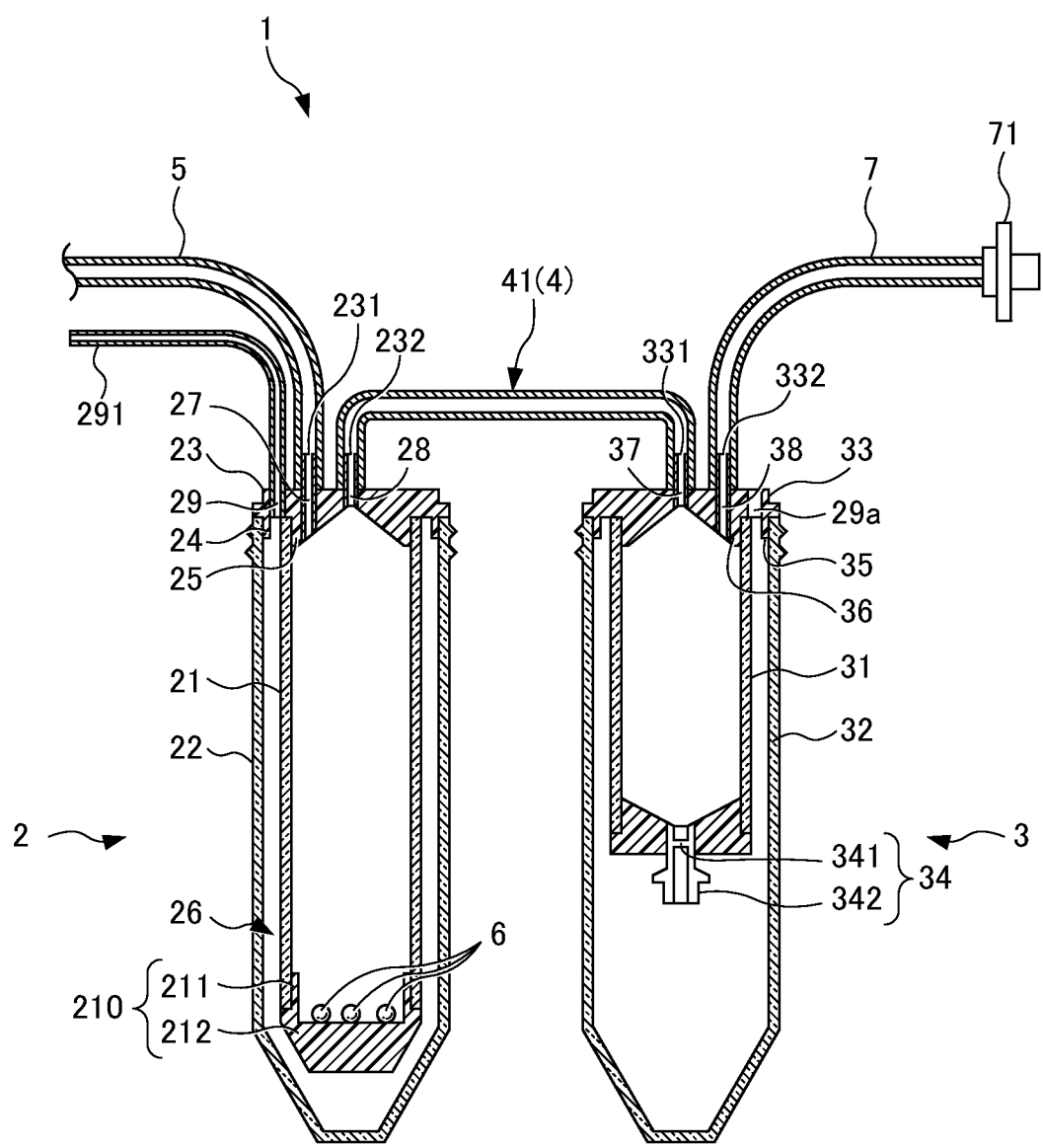
FIG. 7 is a partially expanded view of FIG. 6.

The apparatus 1 for separating and storing blood components of the first embodiment, as shown in FIG. 6 and FIG. 7, is provided with a blood storage part 2 for storing fluid containing at least blood-derived liquid components and platelets; a component storage part 3 for storing at least a part of the components of the fluid stored in the blood storage part; and a linking part 4 aseptically linking the blood storage part 2 and the component storage part 3.

The term "blood" used herein indicates whole blood including hemocytes (erythrocytes, leucocytes, platelets) and plasma (serum) as a liquid component, and a liquid containing at least one of these (for example, blood collected by apheresis). Furthermore, the term "serum" used herein means a pale yellow liquid obtained by allowing collected blood to stand, resulting in a reduction in fluidity, followed by separation from the red coagulated block (clot). The meaning of "serum" according to the present invention is different from common serums in terms of the production process not including separation from the clot, but it means a liquid component in the blood that is useful in cell culture and that includes coagulation factors and growth factors substantially equivalent to those in common serums.

The term "blood derived liquid component" used herein indicates "blood components other than hemocytes" or "mixture of blood components other than hemocytes and an agent such as an anticoagulant added thereto".

The blood storage part 2 uses a blood collecting device 100, as shown in FIG. 7, is provided with a blood storage container 21, a first housing container 22 for housing the blood storage container 21, and a first cap 23 connected to the blood storage container 21 and the first housing container 22.

The blood storage container 21, as shown in FIG. 7, has a longitudinal cylindrical shape, and is formed from a material whose side faces are flexible. Furthermore, a cross section in a radial direction of the blood storage container 21 has an elliptical shape.

A side face of the blood storage container 21 is preferably composed of material that is transparent from a viewpoint in which fluid stored inside the blood storage container 21 is visible. For the flexible material it is possible to use polyvinyl chloride, polyethylene, polypropylene, polyurethane, silicone, ethylene-vinyl acetate copolymer resin, synthetic rubber, and soft synthetic resin such as various types of elastomer. An upper end which is one end of the blood storage container 21 has an opening, and is hermetically sealed by fitting the first cap 23. A bottom cap 210 is fitted to a lower end portion which is the other end of the blood storage container 21, and is joined by an adhesive.

The bottom cap 210 is provided with a cylindrical fitting part 211 and a bottom part 212 contiguous with this fitting part. A cross section in a radial direction of the fitting part 211 has an elliptical shape, and an external diameter thereof is approximately the same as an internal diameter of the blood storage container 21. With regard to the bottom cap 210, the fitting part 211 fits a lower end part of the blood storage container 21. The diameter of the bottom part 212 gradually decreases in a downward direction, after which a bottom face thereof has a flat shape.

The first housing container 22, as shown in FIG. 7, has a cylindrical shape longitudinally similar to the blood storage container 21, and is configured such that its diameter and height are both slightly larger than the blood storage container 21. An upper end which is one end of the first housing container 22 also has an opening, and can be hermetically sealed by fitting the first cap 23. In a vicinity of a lower end portion which is another end of the first housing container 22, the diameter of the first housing container 22 gradually decreases in a downward direction, after which it has an upper-lower reversed conical shape with a flat bottom face on the head thereof.

The first housing container 22 preferably is formed from material that is transparent from a viewpoint in which fluid stored inside the blood storage container 21 is visible, and is preferably formed from material having relatively large rigidity. With regard to the material of which the first housing container 22 is composed, specifically, polycarbonate, polyethylene, polypropylene, polyester, polymethylpentene, methacryl, ABS resin (acrylonitrile butadiene styrene copolymer), PET resin (polyethylene-telephthalate), and hard synthetic resin such as polyvinyl chloride may be cited. The hard synthetic resin refers to synthetic resin having hardness of an extent that does not easily deform due to a pressure variation of an internal space of a container due to injection of fluid to be described later.

A screw ridge is formed on an outer side face in a vicinity of the upper end of the first housing container 22, and a cover cap (not shown in the drawings) having a screw trough corresponding to the screw ridge can be screwed on. By screwing the cover cap onto the first housing container 22, it is possible to prevent the first cap 23 from coming off the first housing container 22 during a blood separation and storing operation, as described later.

The first cap 23 has a flat face with a circular shape, and its diameter is approximately the same as the outer diameter of the first housing container 22 (refer to FIG. 7). The first cap 23, on a lower face that is one face thereof, has a first connecting part 24 that can be connected to the first housing container 22, and a second connecting part 25 that can be connected to the blood storage container 21 on an inner side of the first connecting part 24. The first connecting part 24 and the second connecting part 25 have shapes that protrude in a downward direction.

An outer diameter of the first connecting part 24 is approximately the same as an inner diameter of the opening of the first housing container 22, and the opening vicinity of the first housing container 22 can be fitted to an outer peripheral face of the first connecting part 24. An outer diameter of the second connecting part 25 is approximately the same as an inner diameter of the opening of the blood storage container 21, the opening vicinity of the blood storage container 21 can be fitted to an outer peripheral face of the second connecting part 25.

That is, in the first embodiment, the blood storage container 21 and the first housing container 22 that contains the blood storage container 21 are both configured to be fitted to the first cap 23. The first housing container 22 is hermetically sealed by being fitted to the first cap 23. Furthermore, in this way, a pressure regulating space 26, which is a space independent of an internal space of the blood storage container 21, is formed between an outer side of the blood storage container 21 and an inner side of the first housing container 22.

A hermetically sealing member (not shown in the drawings) for improving sealing of the pressure regulating space 26 is interposed between the outer peripheral face of the first connecting part 24 and an inner peripheral face in the vicinity of the opening of the first housing container 22. In this way, it is possible to ensure a hermetically sealed structure with more certainty for the pressure regulating space 26.

As a hermetically sealing member, it is possible to use, for example, a ring shaped member formed from silicon rubber. The hermetically sealing member may have a configuration which can cap the outer peripheral face of the first connecting part 24; material is not limited to the abovementioned silicon rubber, and it is possible to used elastic members such as various types of rubber, various types of elastomer, and the like.

Furthermore, the hermetically sealing member may be disposed between an outer peripheral face of the second connecting part 25 and an inner peripheral face in the vicinity of the opening of the blood storage container 21.

The blood storage part 2 is provided with a fluid inlet channel 27 for introducing the fluid into the blood storage container 21, and a component outlet channel 28 for extracting at least a part of the components of the fluid from the blood storage container 21. In the first embodiment, the fluid inlet channel 27 and the component outlet channel 28 are arranged in the first cap 23, as shown in FIG. 7. The fluid inlet channel 27 and the component outlet channel 28 are arranged by forming a through hole penetrating the first cap 23 from an upper face thereof to a lower face.

The shape of a portion facing the internal space of the blood storage container 21, with regard to the lower face of the first cap 23, as shown in FIG. 7, is preferably formed to have a gradually decreasing diameter in an upward direction. In addition, a preferable configuration is one in which the component outlet channel 28, which is a through hole in a top part thereof, is provided. With the abovementioned configuration, when serum that is separated inside the blood storage container 21 is extracted to the component storage container 31, it is possible to draw out the serum without waste.

A blood drawing tube 5 is connected to the fluid inlet channel 27, and blood drawn from a subject passes through the blood drawing tube 5 and the fluid inlet channel 27, to be stored aseptically in the blood storage part 2 (the blood storage container 21). The fluid inlet channel 27 and the blood drawing tube 5 are connected by engaging an end part of the blood drawing tube 5 with a first protruding part 231 arranged on an upper face side in a portion in which the fluid inlet channel 27 is formed, in the first cap 23.

The blood storage container 21 contains a blood coagulation promotion substance 6 that is in contact with the fluid and that promotes coagulation of the fluid. The blood coagulation promotion substance 6 is included to an extent such that a blood coagulation factors such as fibrin, platelets, or the like can be activated, and preferably is insoluble in blood. By the blood coagulation promotion substance 6 being insoluble in blood, it is possible to avoid a situation where impurities are mixed in the serum that is obtained.

Furthermore, in a case where the serum is prepared from blood, by activation of factors that are to be activated, such as platelets, blood coagulation factors and the like, centrifuge separation is performed, but from an aspect of suppressing destruction of red blood cells (hemolysis) and damage to the blood storage part, it is preferable that the exterior form of the blood coagulation promotion substance 6 be approximately spherical. In addition, from a viewpoint of rapidly activating the abovementioned factors that are to be activated, a surface of the blood coagulation promotion substance 6 is preferably formed with a layer formed from a compound of silicon dioxide.

At least one type selected from glass, silica, diatomaceous soil, kaolin, or the like can be used as the silicon dioxide compound, but there is no limitation to these. In the first embodiment, approximately spherical glass-formed objects are used as the blood coagulation promotion substance 6.

Setting surface area of the blood coagulation promotion substance 6 inside the blood storage container 21 to have a relationship of 0.1 to 25 $mm^2$/ml with the amount of blood that can be stored in the blood storage container 21 is preferable from aspects of both promotion of activation and suppression of hemolysis.

The blood storage part 2, as shown in FIG. 7, is provided with an injection hole 29 through which fluid can be injected into the pressure regulating space 26. Furthermore, an injection means (not shown in the drawings) that is linked to the injection hole 29 and injects fluid into the pressure regulating space 26 is provided at the injection hole 29. In the first embodiment, the injection hole 29 is arranged in the first cap 23. In detail, the injection hole 29 is a through-hole arranged in the first cap 23, and is formed in an area on an outer side of the second connecting part in the first cap 23 and an inner side of the first connecting part.

One end of a fluid injection tube 291 is connected to the injection hole 29, and an injection means is connected to the other end of the fluid injection tube 291. A pump, syringe, or the like can be used as the injection means.

By injecting fluid from the injection hole 29 by the injection means, the pressure regulating space 26 is pressurized. At this time, since the first housing container 22 forming an outer side of the pressure regulating space 26 is flexible, the blood storage container 21 is affected by the increased pressure of the pressure regulating space 26 and is deformed as if being crushed. Furthermore, the blood storage container 21 that is deformed as if being crushed by the pressurization of the pressure regulating space 26 is restored to its original shape by depressurizing the pressure regulating space 26 that has been pressurized. In this way, by deforming the blood storage container 21 by pressurizing and depressurizing the pressure regulating space 26, it is possible to easily and aseptically extract components of serum, to be described later, into the component storage part 3, and taking of blood.

The fluid that is injected into the pressure regulating space 26 may be a gas such as the air, or may be a liquid such as water. Furthermore, a gel form may be used as the fluid. In a case of using a fluid such as water or a substance in a gel form as the fluid, the volume of the fluid changes due to added pressure at time of injection, and this is preferable in that it is possible to accurately comprehend the amount of serum and the like that is extracted to the component storage part 3.

A linking part 4, as shown in FIG. 7, aseptically links the blood storage part 2 and the component storage part 3. In the first embodiment, the linking part 4 is formed from a linking tube 41, and links the component outlet channel 28 formed in the first cap 23, and the component inlet channel 37 formed in the second cap 33, to be described later. The linking tube 41 and the component outlet channel 28 are connected by engaging one end of the linking tube 41 to a second protruding part 232 provided on an upper face side of a portion in which the component outlet channel 28 is formed in the first cap 23.

The component storage part 3, as shown in FIG. 7, is provided with the component storage container 31, a second housing container 32 that contains the component storage container 31, and the second cap 33 that is joined to the component storage container 31 and the second housing container 32.

The component storage container 31 has a longitudinal cylindrical shape, and is formed from material having a flexible side face. A material similar to the abovementioned blood storage container 21 can be used as the flexible material. An upper end, which is one end of the component storage container 31 has an opening, and is hermetically sealed by being connected to the second cap 33. A component collection part 34 for collecting blood components contained in the component storage container 31 is formed at a lower end part, which is the other end of the component storage container 31.

The component collection part 34 is provided with a component collection orifice 341 formed in a bottom face of the component storage container 31, and a hollow cylindrical part 342 arranged in a lower portion of the component collection orifice 341. The component collection orifice 341 is formed by providing a thin area of a thin film form at a part of a bottom face of the component storage container 31. The cylindrical part 342 protrudes downwards from the bottom face of the component storage container 31, in an area in which the component collecting orifice 341 is formed. The blood components contained inside the component storage container 31 can be collected by breaking and puncturing the component collection orifice 341 with a puncturing tool such as a syringe needle or the like. At this time, since the hollow cylindrical part 342 is formed in an area formed at the component collection orifice 341, it is possible to assuredly puncture the component collection orifice 341 with the puncturing tool.

As shown in FIG. 7, the shape of the bottom face of the component storage container 31 is preferably formed to have a gradually decreasing diameter in a downward direction. In addition, the component collection orifice 341 is preferably arranged at an apex thereof. With the abovementioned configuration, when serum is collected inside the component storage container 31, it is possible to collect the serum that is to be collected, without waste.

Furthermore, distance between the position of the component collection orifice 341 provided in the bottom part of the component storage container 31 and the position of an inner face bottom part of the second housing container 32 is preferably set to a distance whereby the puncturing tool can be contained. With the abovementioned configuration, it is possible to contain the puncturing tool within the second housing container 32 in a state puncturing the component collection orifice 341 of the component storage container 31. If the puncturing tool has an open-close structure, collection and storage of the serum inside the component storage container 31 is possible in accordance with requirements.

The second housing container 32 has a longitudinal cylindrical shape, and is configured such that its diameter and height are both slightly larger than the component storage container 31. An upper end which is one end of the second housing container 32 also has an opening, and can be hermetically sealed by fitting the second cap 33. In a vicinity of a lower end portion which is the other end of the second housing container 32, the diameter of the first housing container 22 gradually decreases in a downward direction, after which it has an upper-lower reversed conical shape with a flat bottom face on the head thereof.

In the first embodiment, the second housing container 32 is formed from material the same as the abovementioned first housing container 22, and the shape and size thereof are the same as the first housing container 22.

A screw ridge, similar to the first housing container 22, is formed on an outer side face in a vicinity of the upper end of the second housing container 32, and a cover cap (not shown in the drawings) having a screw trough corresponding to the screw ridge can be screwed on.

The second cap 33, similar to the first cap 23, has a flat face with a circular shape, and its diameter is approximately the same as the outer diameter of the second housing container 32. The second cap 33 on a lower face, which is one face thereof, has a third connecting part 35 that can be connected to the second housing container 32, and a fourth connecting part 36 that can be connected to the component storage container 31 on an inner side of the third connecting part 35. The third connecting part 35 and the fourth connecting part 36 have shapes that protrude in a downward direction.

An outer diameter of the third connecting part 35 is approximately the same as an inner diameter of the opening of the second housing container 32, and the opening vicinity of the second housing container 32 can be fitted to an outer peripheral face of the third connecting part 35. An outer diameter of the fourth connecting part 36 is approximately the same as an inner diameter of the opening of the component storage container 31, the opening vicinity of the component storage container 31 can be fitted to an outer peripheral face of the fourth connecting part 36.

As shown in FIG. 7, a through hole 29a is provided in the second cap 33, but this through hole 29a need not be provided.

That is, in the first embodiment, the component storage container 31 and the second housing container 32 that contains the component storage container 31 are both configured to be fitted to the second cap 33. The component storage container 31 is hermetically sealed by being fitted to the second cap 33, and the second housing container 32 is also hermetically sealed by being fitted to the second cap 33.

The component storage part 3 has a component inlet channel 37 for introducing at least a part of the components of the fluid that have been drawn from the blood storage container 21. In the first embodiment, as shown in FIG. 7, the component inlet channel 37 is arranged in the second cap 33. The component inlet channel 37 is provided by forming a through hole penetrating the second cap 33 from a top face thereof to a bottom face.

The linking tube 41 is connected to the component inlet channel 37, and serum drawn from the blood storage container 21 is stored aseptically within the component storage part 3 (the component storage container 31). The component inlet channel 37 and the linking tube 41 are connected by engaging an end part of the linking tube 41 with a third protruding part 331 arranged on an upper face side in a portion in which the fluid inlet channel 37 is formed, in the second cap 33.

A ventilation channel 38 for air circulation to and from the component storage container 31 is provided in the component storage part 3, and a ventilation tube 7 provided with a ventilation filter 71 is further linked to the ventilation channel 38. In the first embodiment, the ventilation channel 38 is provided in the second cap 33. In detail, the ventilation channel 38 is a through hole provided in the second cap 33, and is formed in an area on an inner side of the fourth connecting part 36 in the second cap 33.

One end of the ventilation tube 7 is connected to the ventilation channel 38, and the ventilation filter 71 is connected to the other end of the ventilation tube 7. The ventilation filter 71 is a filter having a property by which air is passed but fluid is not passed, and bacteria are also not passed. That is, the ventilation filter 71 can aseptically circulate air to and from the inside the component storage container 31, from the linked ventilation channel 38. The ventilation channel 38 and the ventilation tube 7 are connected by engaging an end part of the ventilation tube 7 to a fourth protruding part 332 provided on an upper face side of a portion in which the ventilation channel 38 is formed in the second cap 33.

In the blood component separation and storage apparatus 1 of the first embodiment having the abovementioned configuration, the blood storage part 2 (the blood storage container 21), the linking part (the linking tube 41), and the component storage part 3 (the component storage container 31) are aseptically linked, and internal spaces in each of the blood storage container 21, the linking tube 41, and the component storage container 31 are kept in an aseptic state. As a result, by circulating air aseptically to and from the ventilation channel 38, the blood component separation and storage apparatus 1 of the first embodiment can regulate the internal spaces in each of the blood storage container 21, the linking tube 41, and the component storage container 31, to an arbitrary pressure while aseptically maintaining an aseptic state.

Next, a description will be given concerning a preferable size of each component member in the blood component separation and storage apparatus 1 of the first embodiment.

A stored amount of blood in the blood storage container 21 is preferably from 5 to 200 ml, and more preferably 5 to 50 ml. The blood storage container 21 specifically has a preferable internal diameter of 10 to 30 mm, and a preferable height thereof is 50 to 150 mm.

The stored amount of blood components in the component storage container 31, from the viewpoint that liquid components separated from the blood stored in the blood storage container 21 are assuredly stored, is preferably 40 to 100% of the blood storage amount in the blood storage container 21.

If the first housing container 22 and the second housing container 32 are of sizes that can respectively contain the blood storage container 21 and the component storage container 31, there is no particular limitation on size, but diameters thereof are preferably 10 to 30 mm, and heights thereof are preferably 50 to 150 mm.

Furthermore, well known centrifuge separating tubes are preferably used as the first housing container 22 and the second housing container 32. By using the well known centrifuge separating tubes as the first housing container 22 and the second housing container 32, in a centrifuge separation step in a blood component separation operation described below, it is possible to perform the separation operation simply by using a normal centrifuge separator in which the centrifuge separating tube can be used.

When well known centrifuge separating tubes are used as the first housing container 22 and the second housing container 32, the volume of the centrifuge separating tubes, from the viewpoint of raising general usability in the centrifuge separation process, is preferably 5 to 50 ml.

Next, using FIG. 8 to FIG. 13 a description is given concerning one preferred mode of a blood component separation storing operation using the blood component separation and storage apparatus 1 of the first embodiment having the abovementioned configuration.

Figure 8:
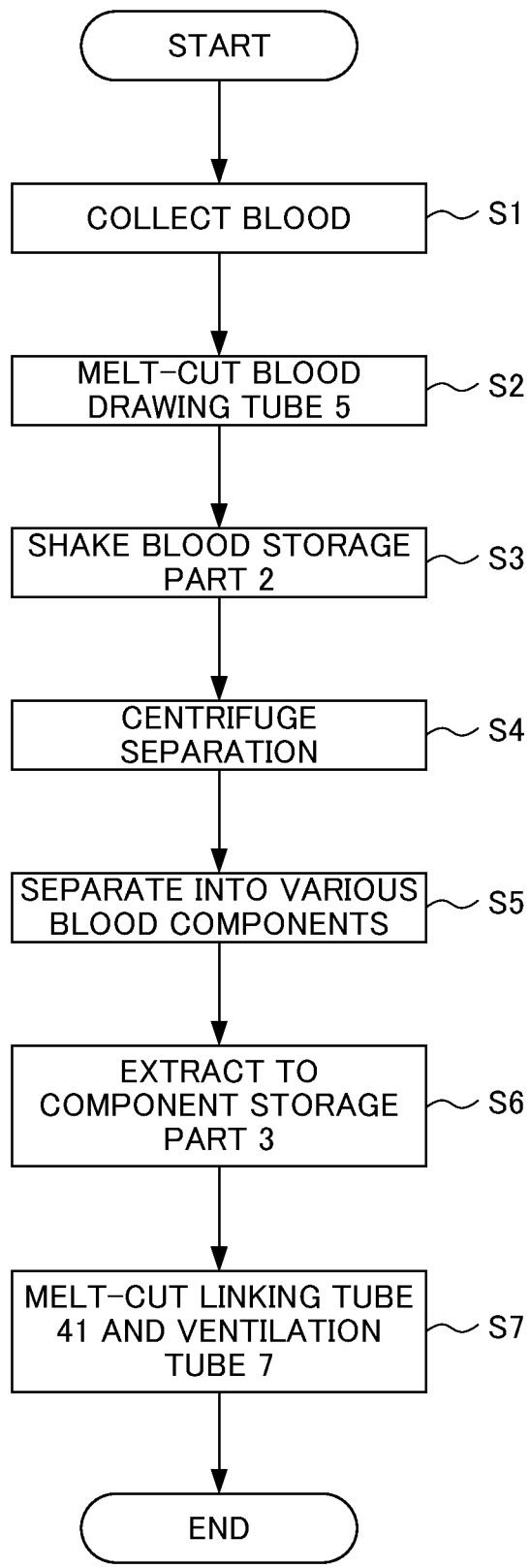
FIG. 8 is a drawing showing a procedure for separating and storing blood components using the blood component separation and storage apparatus of the first embodiment.
Figure 9:
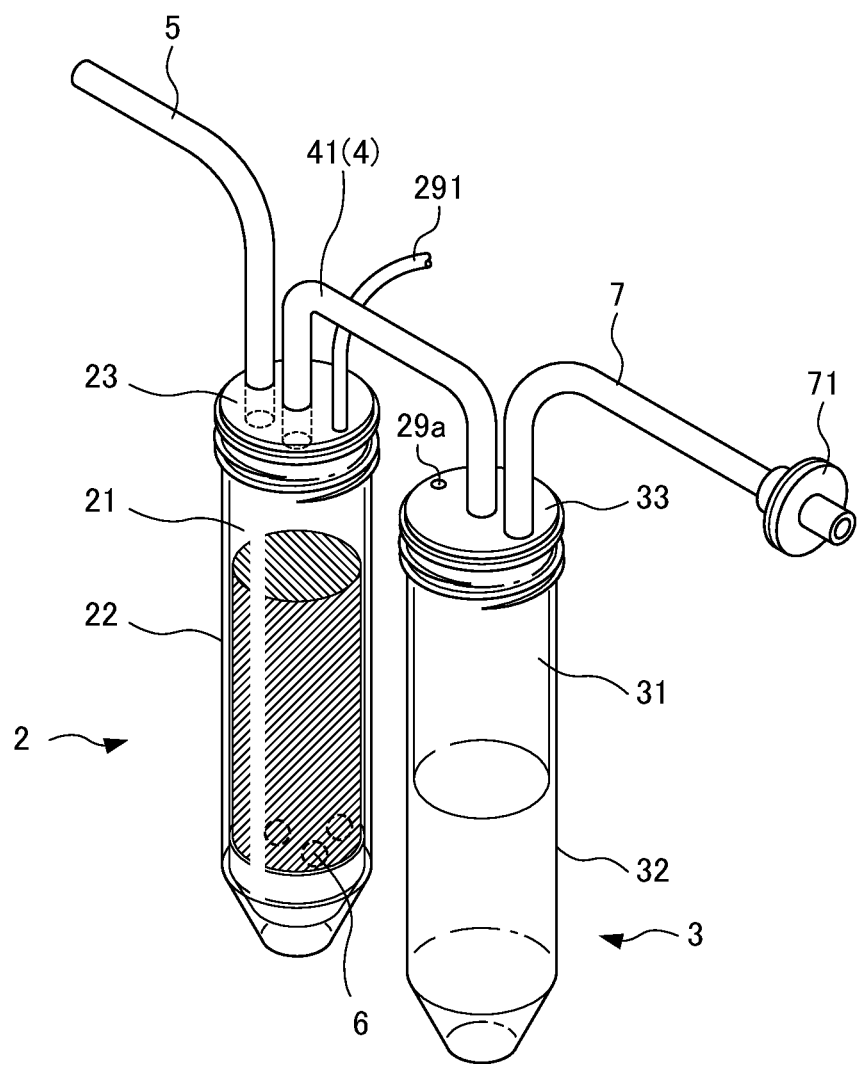
FIG. 9 is a drawing showing a storage step in an operation of separating and storing blood components using the blood component separation and storage apparatus of the first embodiment.

As shown in FIG. 8, the blood component separation storing operation of the present mode is generally made up of 7 steps (S1 to S7).

First, in a storage step S1, as shown in FIG. 6, a blood drawing needle 80 is inserted into a subject (patient), and blood is drawn. At this time, the blood drawn by the blood drawing needle 80 is stored inside a blood storage part 2 (blood storage container 21), via a blood drawing tube 5 (refer to FIG. 9). When the blood is collected, by drawing in air from a ventilation filter 71 located at an extremity of a ventilation tube 7 provided in a component storage part 3, a negative pressure is applied inside a component storage container 31 and a blood storage container 21 communicating thereto, and it is possible to simply draw blood into the blood storage part 2. Furthermore, a non-return valve (not shown in the drawing) for preventing blood from back-flowing to the subject while blood is being drawn may be provided.

In addition, after the storage step S1, so that the blood collected in the blood storage part 2 does not flow towards the component storage part 3, a path of a linking tube 41 is closed at a source side of the blood storage part 2 by using a clamp (not shown in the drawings) or the like. In the storage step S1, consideration is given to the physical condition of a patient when blood is taken, a required amount is collected, and the step is completed. The required amount referred to here is approximately 5 to 50 ml when there is no problem with the patient's body size and condition.

After the storage step S1, the blood needle 80 is withdrawn from the subject of the blood collection, a part of the blood drawing tube 5, which connects the blood drawing needle 80 and the blood storage part 2, is melt-cut, and at the same time the melt-cut end is melted (melt-cut step S2). What is called a melting cutter (not shown in the drawings) referred to as a sealer can be used in melt-cutting the drawing tube 5.

Figure 10:
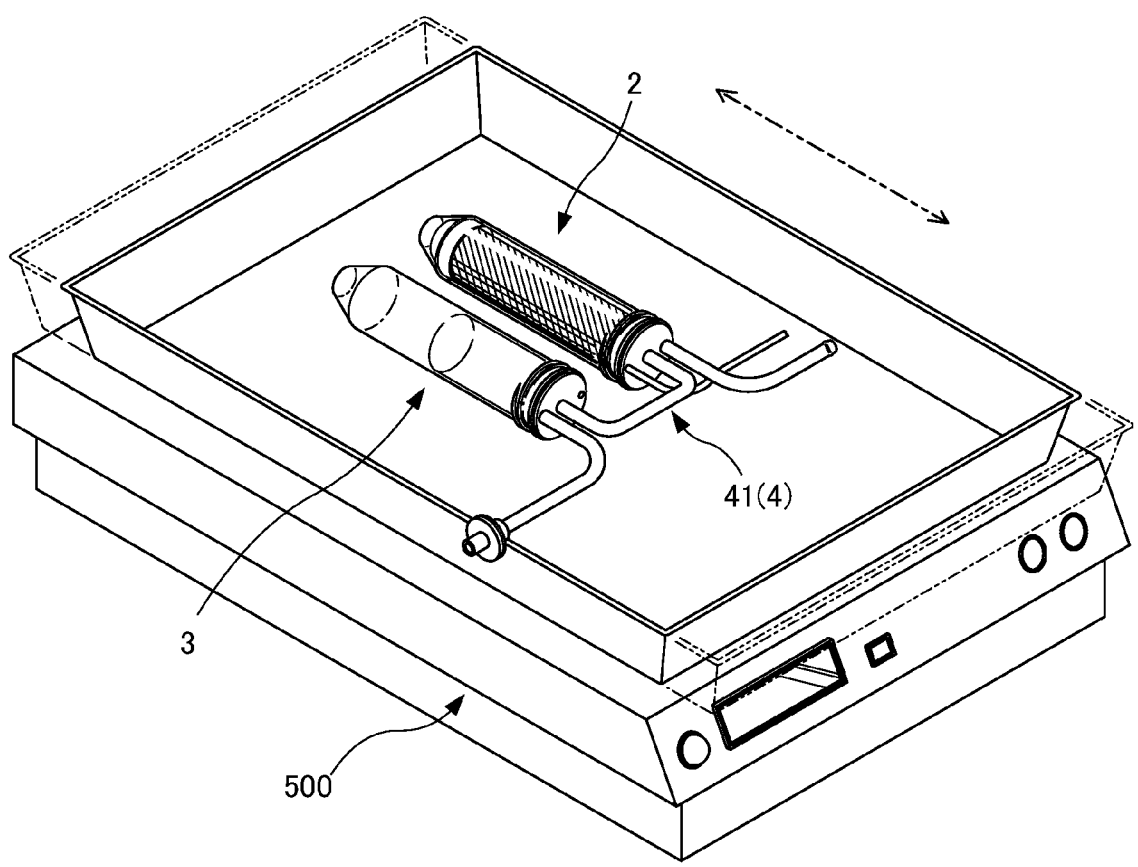
FIG. 10 is a drawing showing an activation promotion step in the operation of separating and storing blood components using the blood component separation and storage apparatus of the first embodiment.

Next, as shown in FIG. 8 and FIG. 10, after completing the storage step S1, the blood storage part 2 is shaken (activation promotion step S3). In the activation promotion step S3, the blood storage part 2, which stores the blood that has been collected, is agitated gently by a shaking device 500, and contact is made with a blood coagulation promotion substance 6 that is housed inside the blood storage container 21. Platelets and coagulation factors included in the blood are activated at the surface of the blood coagulation promotion substance 6, and growth factors coming from the platelets that have been activated are emitted therefrom.

Figure 11:
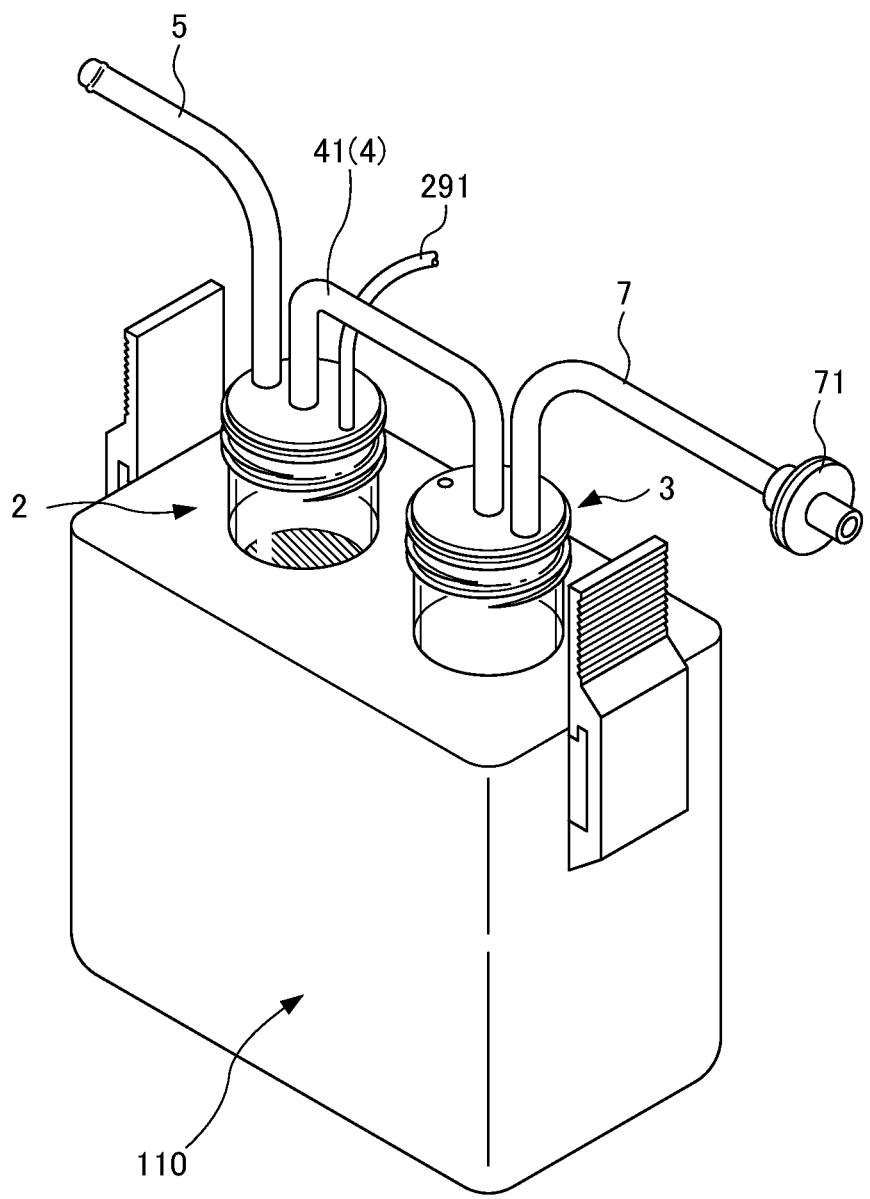
FIG. 11 is a drawing showing a state in which a blood component separation and storage container is housed in a centrifuge holder, in a centrifuge step in the operation of separating and storing blood components using the blood component separation and storage apparatus of the first embodiment.

A centrifuge separator is applied to the blood storage part 2, which has been separated from the subject whose blood was collected after the activation promotion step S3 was done, together with the component storage part 3, the linking tube 41, the ventilation tube 7, and the like (centrifuge separation step S4). At this time, with the blood storage part 2 (the first housing container 22) and the component storage part 3 (the second housing container 32), in a case of using a well known centrifuge separation tube, as shown in FIG. 11, the blood storage part 2 and the component storage part 3 are inserted in a centrifuge holder 110 used for the centrifuge separator, and it is possible to perform centrifuge separation simply. The linking tube 41 is maintained in a state in which a path is closed by a clamp or the like (not shown in the figure) similar to the storage step S1.

A condition of the centrifuge separation with respect to the blood storage part 2 is that a setting is made according to the amount of blood stored and the type of components separated, and a setting is made, for example, to 2250 g×10 minutes at 4° C.

Figure 12:
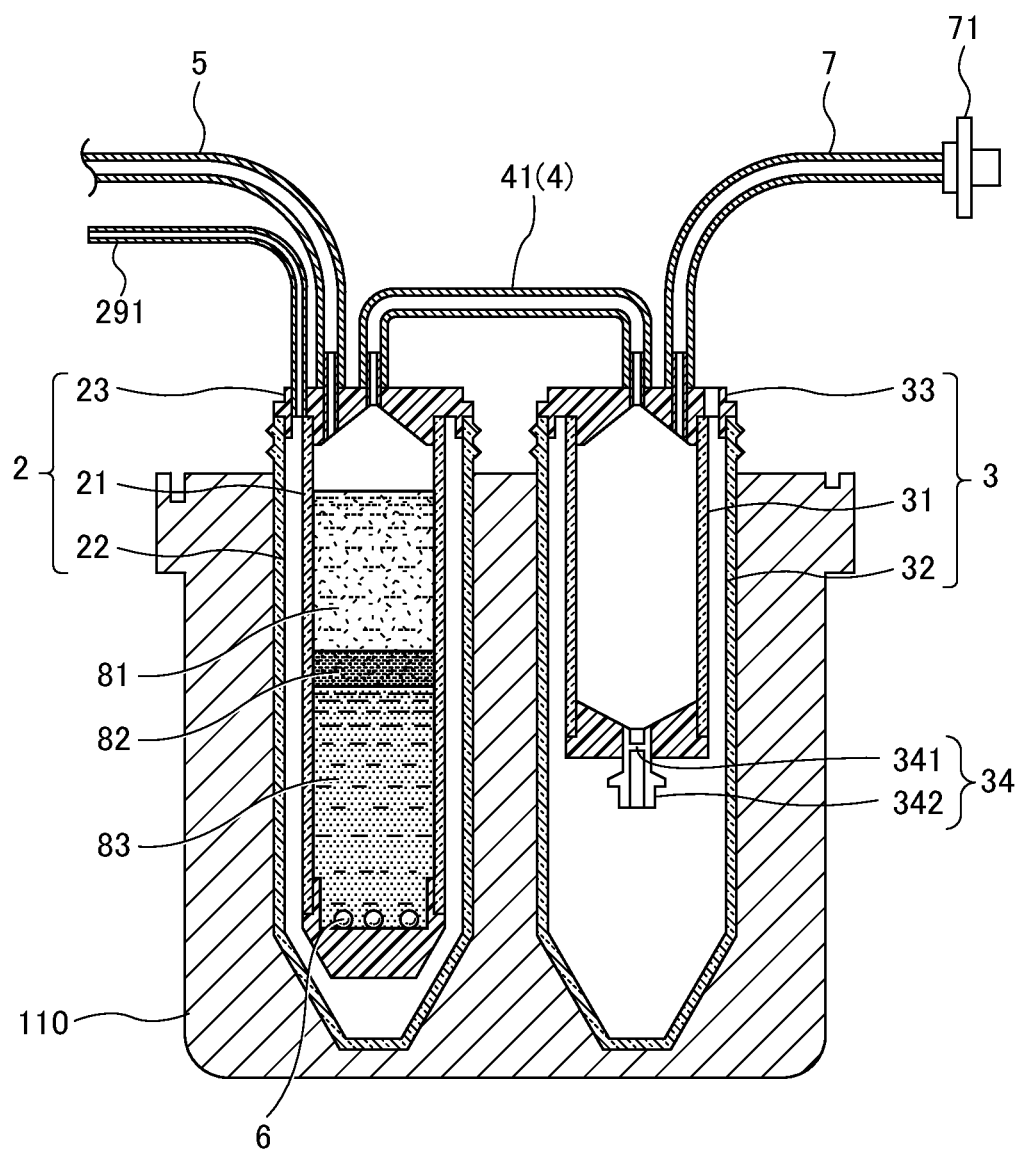
FIG. 12 is a drawing showing a state before a pressure regulating space is pressurized, in a step of separating the blood components in an operation of separating and storing blood components using the blood component separation and storage apparatus of the first embodiment.

The blood that has undergone centrifuge separation after the activation promotion step S3 has been done, is generally separated and fractioned into 3 layers of serum 81, white blood cells 82, and red blood cells 83, inside the blood storage part 2 (the blood storage container 21), as shown in FIG. 12. Furthermore, the blood coagulation promotion substance 6 sinks to the bottom of the blood storage container 21, in a state where coagulated bodies of the platelets and the coagulation factors are attached to the surface thereof.

The serum obtained after passing through the activation promotion step S3 and the centrifuge separation step S4, as described above, includes growth factors originating from the blood platelets and the coagulation factors adequately emitted in the activation promotion step S3.

The factors to be activated such as the platelets and the coagulation factors that have been activated in the activation promotion step S3 and the centrifuge separation step S4 attach to the surface of the blood coagulation promotion substance 6, form aggregates, and are separated from the blood (separation step S5).

Figure 13:
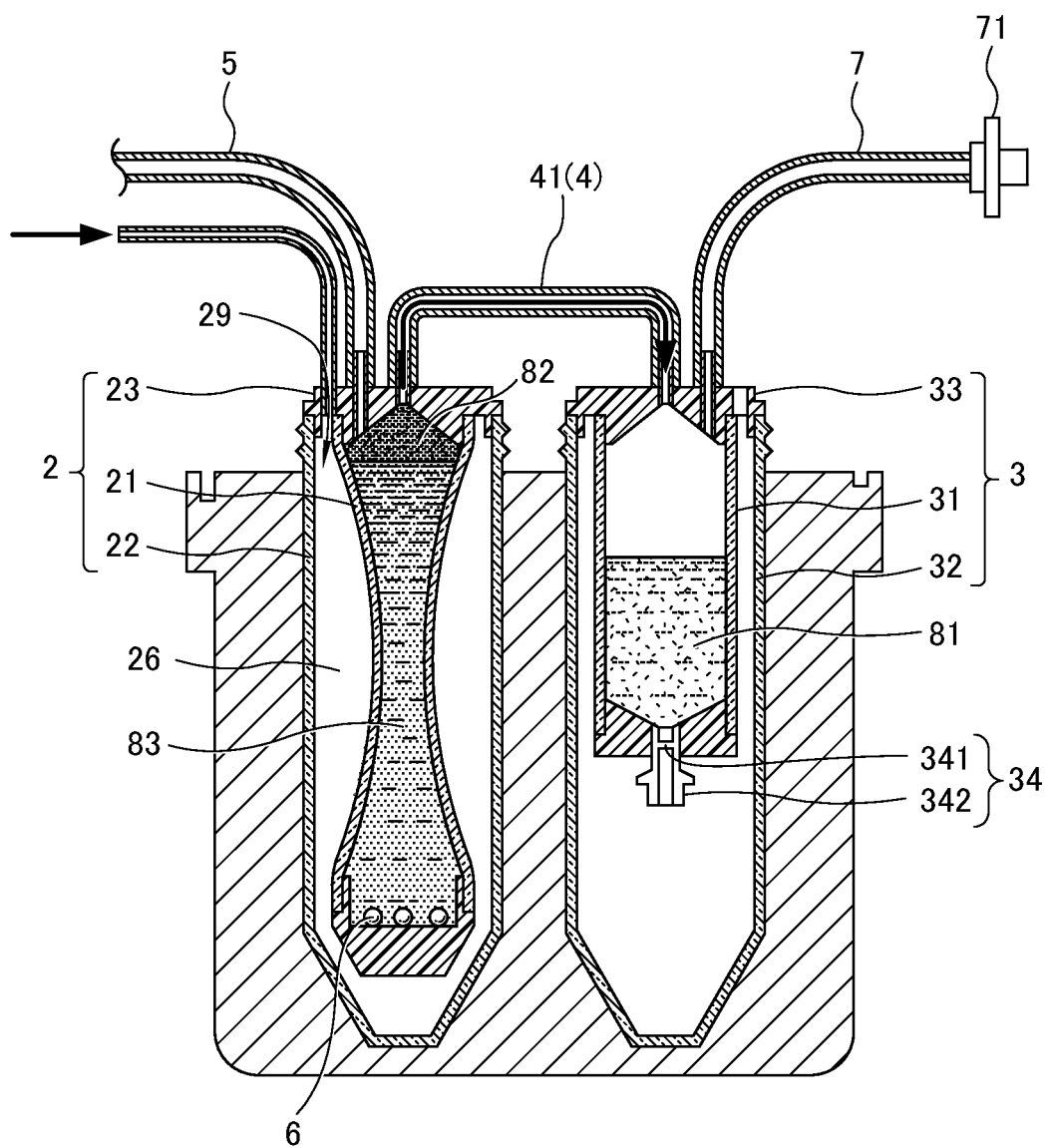
FIG. 13 is a drawing showing a state in which the pressure regulating space is pressurized, in a step of separating the blood components in an operation of separating and storing blood components using the blood component separation and storage apparatus of the first embodiment.

As shown in FIG. 13, in an extraction step S6, the serum 81 that was separated inside the blood storage container 21 in the separation step S5 is extracted to the component storage container 31 in the component storage part 3.

When the serum 81 separated inside the blood storage container 21 is extracted to the component storage container 31, as shown in FIG. 13, first the pressure regulating space 26 is pressurized by injecting fluid from the injection hole 29 to the pressure regulating space 26 formed between the blood storage container 21 and the first housing container 22 in the blood storage part 2. A pump, syringe, or the like can be used as the injection means for injecting the fluid, and a gas such as the air, a fluid such as water, or a substance in a gel form can be used as the fluid. Here, since the first housing container 22 forming an outer side of the pressure regulating space 26 is relatively rigid, the blood storage container 21, which has flexibility, is affected by increased pressure of the pressure regulating space 26 and deforms as if being crushed; the serum 81, which is supernatant that has been separated, is extracted via the linking tube 41 from the component outlet channel 28, and is drawn into the component storage part 3 (the component storage container 31).

In the extraction step S6, along with pressurization of the pressure regulating space 26 as described above, air may be drawn in from the ventilation filter 71 positioned at an extremity of the ventilation tube 7 provided in the component storage part 3. By drawing air from the ventilation filter 71, a negative pressure is applied inside the component storage container 31 and the linking tube 41 communicating therewith, and it is possible to draw the serum 81 from the blood storage container 21 to the component storage container 31 more easily.

After the component storage container 31 has been filled with the required amount of serum, the linking tube 41 and the ventilation tube 7 are melt-cut and melted (melt-cutting step S7). With regard to this melt-cut and melting, a method can be used that is the same as that of melt-cutting and melting the drawing tube before the centrifuge separation step S4. After the melt-cutting step S7, by performing what is referred to as an inactivation process (heating to 56° C. for 30 minutes) on the component storage container 31 that contains the serum, it is possible to inactivate complements within the serum. Furthermore, preservation treatment such as cryopreservation is applied to the component storage container part 3 which has been filled with serum inside the component storage container 31. Here, since the second housing container 32 containing the component storage container 31 is formed from a hard synthetic resin, when the contained serum is being transported and stored, it is possible to prevent the component storage container 31 from being damaged even if external force acts on the component storage part 3. Furthermore, when the component storage part 3 is stored, it is possible to easily attach a label or the like describing information concerning the contained contact.

According to the blood component separation and storage apparatus 1 of the first embodiment having the abovementioned configuration, since the blood storage part 2 has the blood storage container 21 that has a cylindrical form and is flexible, it is possible to separate blood components more simply. Furthermore, since the blood storage part 2, the component storage part 3, and the linking part 4 that links these are connected aseptically, the blood or the serum is not affected by the external environment, the danger of the prepared serum being contaminated by microbes or the like is low, and it is possible to prepare the serum with a high degree of safety.

Furthermore, by the blood storage container 21 having a longitudinal cylindrical shape, even with a relatively small amount of blood collected, it is possible to easily separate the blood components, and it is possible to easily extract the separated components from the blood storage container 21. The ability to easily separate and store blood components even with a relatively small amount of blood in this way is particularly effective when preparing serum from the blood of a subject for which the amount of blood that can be drawn is limited. Here, a relatively small amount of blood indicates, in specific terms, a blood amount of approximately from 5 to 50 ml.

storage container 21 and the first housing container 22 in the blood storage part 2 and the injection hole 29 for injecting the fluid into the pressure regulating space, it is possible to pressurize the pressure regulating space 26 and to deform the blood storage container 21 as if it were being crushed. In this way, by deforming the blood storage container 21 by pressurizing the pressure regulating space 26, it is possible to easily and aseptically draw the components of the serum and the like to the component storage part 3.

Furthermore, the blood storage container 21 that is deformed as if being crushed by pressurization of the pressure regulating space 26 is restored to its original shape by depressurizing the pressurized pressure regulating space 26. Therefore, before drawing blood the blood storage container 21 is deformed as if being crushed by pressurization of the pressure regulating space 26, and when blood is being drawn, the blood storage container 21 is restored to its original shape by depressurizing the pressure regulating space 26, and it is possible to easy draw blood with the inside of the blood storage container 21 having negative pressure.

In addition, a radial cross section of the blood storage container 21 has an elliptical shape. In this way, the blood storage container 21 deforms easily in the short axial direction of the elliptical shape, and it is possible to easily draw the components of the serum and the like to the component storage part 3.

Furthermore, by the first housing container in the blood storage part 2 and the second housing container 32 in the component storage part 3 having a longitudinal cylindrical shape, postural maintenance of the blood component separation and storage apparatus 1 that includes the blood storage part 2 and the component storage part 3 becomes easy, and operability of the blood component separation container is improved. Furthermore, with the first housing container 22 and the second housing container 32 having the same shape and having a prescribed shape, storage is possible in an ordinarily used centrifuge holder, without using a special support device, application is possible to the centrifuge separator, and the general applicability of the blood component separation and storage apparatus 1 is improved. In addition, by containing the blood storage part 2 and the component storage part 3 in the centrifuge holder, since the disposition of the blood component separation and storage apparatus 1 can be maintained, it is possible to use the centrifuge holder as an operational support device that can be commonly used in a series of steps extending from the blood storage step S1 to the melt-cutting step S7. The prescribed shape refers to cases of, for example, a shape similar to a 50 ml commercially available centrifuge settling tube.

Furthermore, since the blood coagulation promotion substance 6 is contained in the blood storage container 21, blood clots adhere to the surface of the blood coagulation promotion substance 6 when the serum is prepared, and mixing of blood clots and fibrin into the serum when the serum is separated is prevented.

Next, a description is given concerning a second embodiment of the blood component separation and storage apparatus 1 of the present invention. In the second embodiment, the description will be mainly about points of difference from the above described first embodiment, and items are given the same reference symbols and descriptions thereof are omitted. For points that are not described in particular, descriptions concerning the first embodiment are applicable as appropriate.

The blood component separation and storage apparatus 1 of the second embodiment differs from the first embodiment in that, in addition to an injection hole 29 provided in a blood storage part 2, a second injection hole 29a is provided in a component storage part 3.

Figure 14:
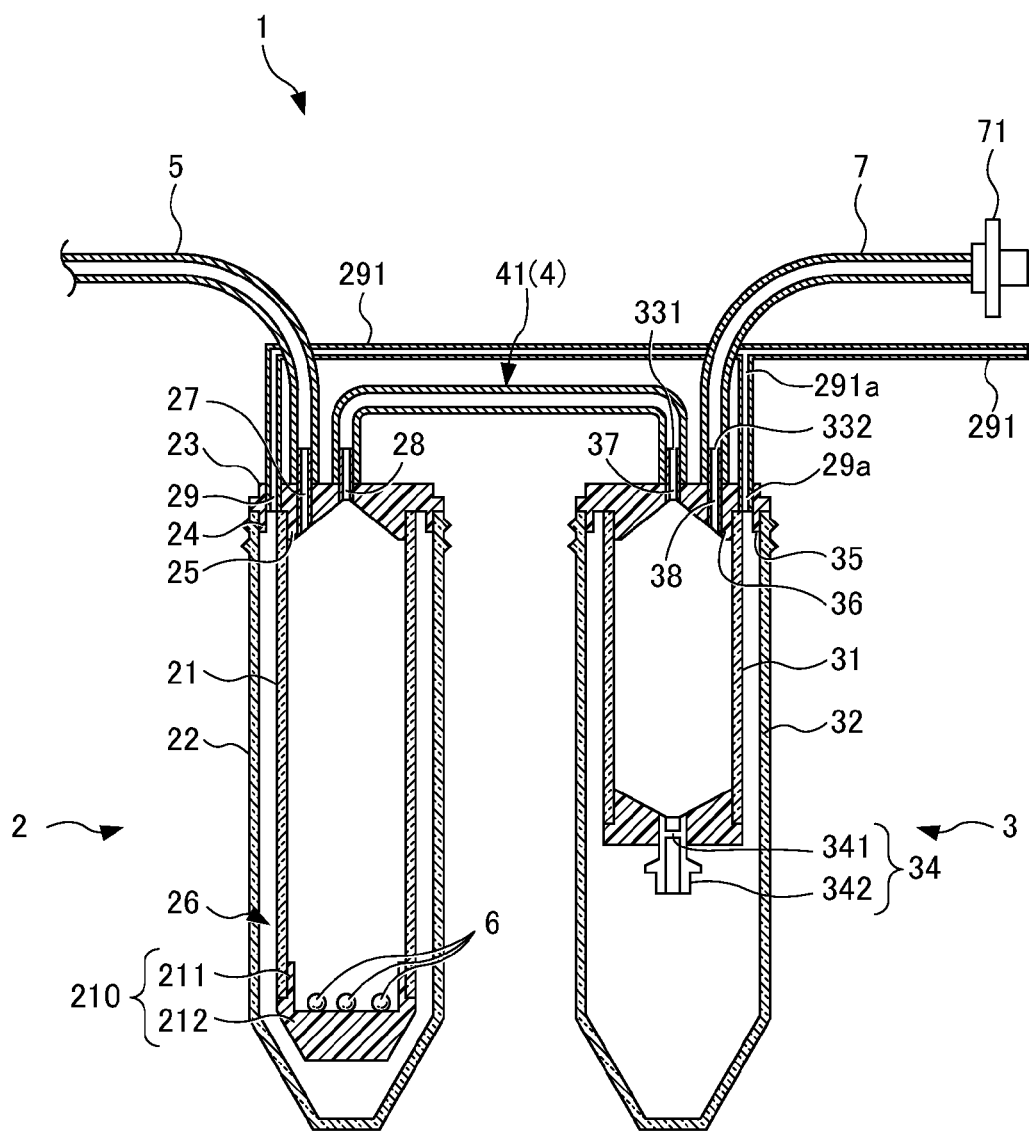
FIG. 14 a partially expanded view showing a second embodiment of the blood component separation and storage apparatus.

In the blood component separation and storage apparatus 1 of the second embodiment, the component storage part 3, as shown in FIG. 14, is provided with the second injection hole 29a that can inject fluid into a space provided between an outer face of a component storage container 31 and an inner face of a second housing container 32. In the second embodiment, the second injection hole 29a is provided in a second cap 33. In detail, the second injection hole 29a is a through hole provided in the second cap 33, and is formed on an outer side of a fourth connection part 36 in the second cap 33 and in a region of an inner side of a third connection part 35. One end of a second fluid injection tube 291a is connected to the second injection hole 29a. The other end of the second fluid injection tube 291a is linked to a prescribed position between two ends of a fluid injection tube 291, one end of which is connected to the injection hole 29 and the other end of which is connected to a fluid injection means (not shown in the drawings).

According to the blood component separation and storage apparatus 1 of the second embodiment, by injecting fluid into a space formed between the outer face of the component storage container 31 and the inner face of the second housing container 32 in the component storage part 3, it is possible to regulate the pressure not only of a pressure regulating space 26 in the blood storage part 2, but also inside a space formed between the outer face of the component storage container 31 and the inner face of the second housing container 32. Therefore, for example, when blood is drawn in a blood storage step S1, when a negative pressure is applied inside the component storage container 31 and inside the blood storage container 21 communicating thereto by drawing air from a ventilation filter 71, by drawing fluid from the injection hole 29 and the second injection hole 29a by the fluid injection means together with drawing from the ventilation filter 71, it is possible to apply a negative pressure also to the space formed between the outer face of the component storage container 31 and the inner face of the second housing container 32, and to the pressure regulating space 26 in the blood storage part 2. In this way, by applying a negative pressure to both the space formed between the outer face of the component storage container 31 and the inner face of the second housing container 32, and to the pressure regulating space 26 together with drawing air from the ventilation filter 71, it is possible to prevent the component storage container 31 and the blood storage container 21 from being crushed due to drawing of air from the ventilation filter 71, and it is possible to prevent a decrease in an effect of drawing blood to the blood storage part 2.

The present invention has been described above based on preferred embodiments and modes, but the present invention is not limited to the abovementioned embodiments and modes and changes that do not depart from the scope of the invention are possible as appropriate.

For example, the connection between the first cap 23 and the blood storage container 21 or the first housing container 22, and the connection between the second cap 33 and the component storage container 31 or the second housing container 32 in the first embodiment and the second embodiment is by mating, but these connections may be, for example, by screwing together.

Furthermore, in the first embodiment and the second embodiment, a hermetically sealed member is interposed between the first cap 23 and the first housing container 22, but there is no limitation to this, and the hermetically sealed member may be interposed between the second cap 33 and the component storage container 31.

In addition, in the first embodiment and the second embodiment, the lower end part of the blood storage container 21 is formed from the bottom cap 210, but the lower end part of the blood storage container 21 may be formed by welding and sealing a flexible member forming a side face, at the lower end part.

Furthermore, the bottom cap 210 may be formed by a flexible member forming a side face.

In this way, by forming the bottom cap 210 by a member that has flexibility, the blood storage container 21 deforms easily in the bottom end part due to pressurization of the pressure regulating space 26, and it is possible to easily extract components such as serum or the like into the component storage part 3.

Furthermore, in the second embodiment, the fluid injection tube 291 and the second fluid injection tube 291a are linked together, but the two need not be linked. In addition, the fluid injection tube 291, the second fluid injection tube 291a, and the ventilation tube 7 may be linked.

Moreover, the blood coagulation promotion substance 6 in the first embodiment and the second embodiment is a glass-formed object, but air may be used instead of the glass-formed object, or the glass-formed object and air may be used together.

Furthermore, transport of serum from the blood storage container 21 to the component storage container 31 in the first embodiment and the second embodiment is performed by deforming the blood storage container 21 by pressurizing the pressure regulating space, but the blood storage container 21 may be deformed by applying a negative pressure inside the component storage container 31 and the blood storage container 21 that communicates therewith, by drawing air from a ventilation channel.

In addition, the injection hole 29 in the first embodiment and the second embodiment is provided in the first cap 23, but may be provided on a side face of the first housing container 22.

Furthermore, the lower end parts of the blood storage container 21 and the component storage container 31 in the first embodiment and the second embodiment are configured to be at a distance from the respective inner sides of the first housing container 22 and the second housing container 32, but a configuration is also possible in which the two members are fixed by coming into contact or by means for mating together.

In addition, a configuration is possible in which a spacer (not shown in the drawings) is disposed between the lower end part of the blood storage container 21 and the bottom part of the first housing container 22, and between the lower end part of the component storage container 31 and the second housing container 32.

With the abovementioned configuration, in the centrifuge separation step in a blood component separation operation of the present apparatus, it is possible to reduce load placed on each of the blood storage container 21 and the component storage container 31.

Furthermore, the shape of a portion facing an internal space of the component storage container 31 at a lower face of the second cap 33, in the first embodiment and the second embodiment, as shown in FIG. 7 and FIG. 14, is configured with a form that gradually decreases in diameter in an upward direction, and the component inlet channel 37, which is a through hole, is arranged at an apex thereof.

Figure 15:
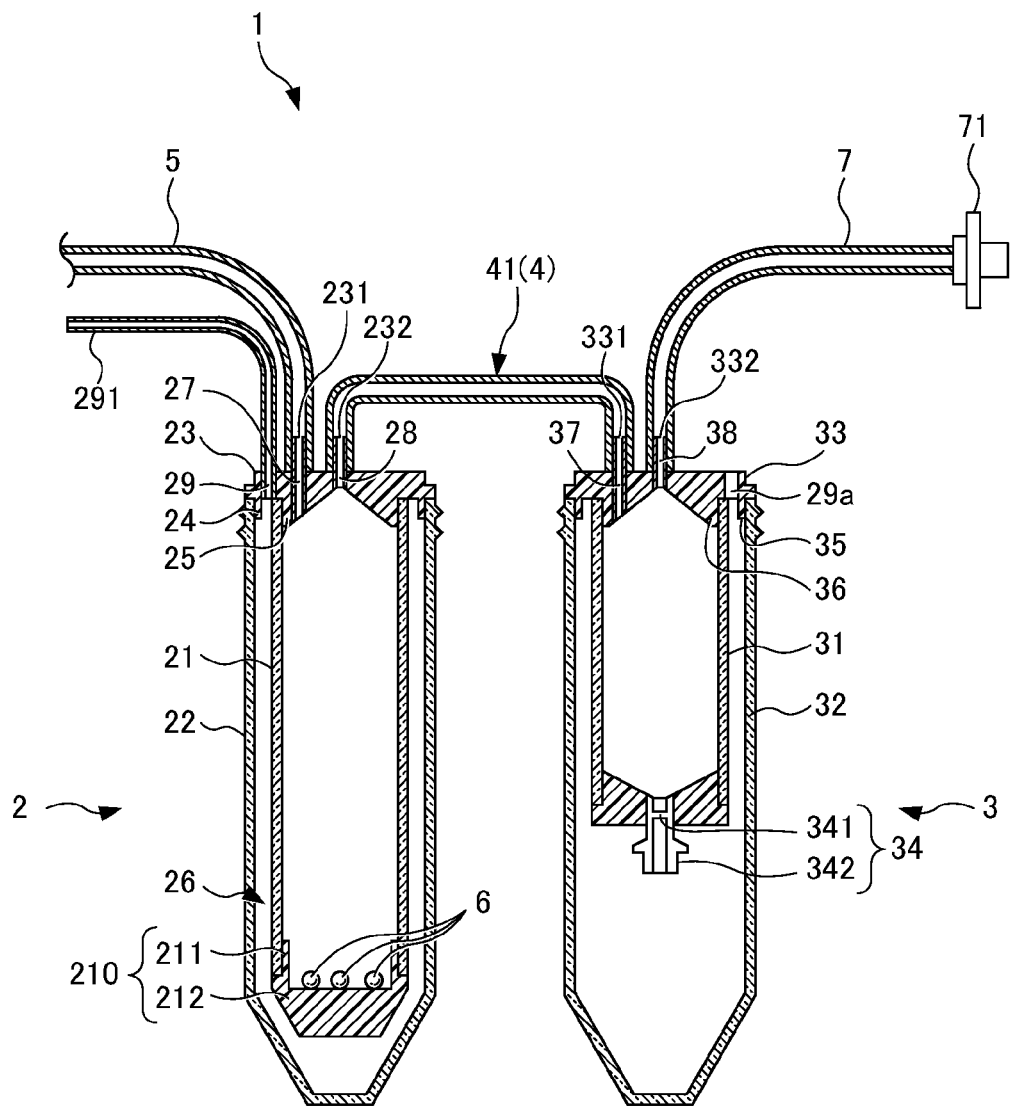
FIG. 15 is a view showing a modified example of the blood component separation and storage apparatus of the first embodiment.

However, the present configuration may be configured such that the ventilation channel 38, which is a through hole, is arranged at an apex of the second cap 33 (refer to FIG. 15).

In this way, when air is drawn from the ventilation channel 38 to perform an operation of depressurizing inside the component storage container 31, it is possible to perform the operation of depressurization, without drawing components (for example, serum) contained inside the component storage container 31.

Furthermore, a blood cell removing filter (not shown in the drawings) may be interposed in an empty portion of any of the component outlet channel 28, the linking tube 41 or the component inlet channel 37. In this way, blood cell components in the blood storage container 21 can be captured by the blood cell removing filter, and it is possible to prevent mixing of the blood cell components into the component storage container 31.

The invention claimed is:

1. A liquid component collecting device comprising:
   a flexible cylindrical liquid component storage container having a first opening and a second opening at one end;
   a rigid cylindrical first housing container for housing the liquid component storage container therein and having an opening at one end;
   a pressure regulating space formed between an outer side of the flexible liquid component storage container and an inner side of the rigid first housing container, the pressure regulating space being hermetically sealed from an internal space of the liquid component storage container and from an external environment of the liquid component collecting device; and
   a first cap configured to hermetically seal the internal space of the liquid component storage container and the pressure regulating space from each other and from the external environment, the first cap comprising:
      a liquid component inlet channel engaged with the first opening of the liquid component storage container and configured to allow passage of a liquid component therethrough,
      a first communication channel engaged with the second opening of the liquid component storage container and configured to communicate with the internal space of the liquid component storage container, and
      a second communication channel engaged with the opening of the rigid first housing container and configured to communicate with the pressure regulating space so as to regulate an internal pressure of the pressure regulating space between a high pressure state, wherein the flexible liquid component storage container is deformed as if being crushed, and a low pressure state, wherein the pressure regulating space is configured for restoring of the deformed liquid component storage container into its original condition, thereby drawing the liquid component through the liquid component inlet channel.

2. The liquid component collecting device according to claim 1, wherein a ventilation tube comprising a ventilation filter is linked to the first communication channel.

3. The liquid component collecting device according to claim 1, further comprising a depressurizing unit linked to each of the first communication channel and the second communication channel.

4. The liquid component collecting device according to claim 1, further comprising an injection unit linked to the second communication channel, wherein the injection unit is configured to inject fluid into the pressure regulating space thereby generating the high pressure state of the pressure regulating space, and is configured to withdraw fluid from the pressure regulating space thereby generating the high pressure state of the pressure regulating space.

5. The liquid component collecting device according to claim 1, wherein a cross section in a radial direction of the liquid component storage container has an elliptical shape.

6. The liquid component collecting device according to claim 1, further comprising a first liquid component collecting unit at another end of the liquid component storage container, wherein the first liquid component collecting unit is configured for collecting a liquid component stored in the liquid component storage container.

7. The liquid component collecting device according to claim 6, wherein the first cap further comprises a second liquid component collecting unit, the second liquid component collecting unit configured for collecting a liquid component stored in the liquid component storage container.

8. The liquid component collecting device according to claim 1, further comprising a blood coagulation accelerating substance disposed in the internal space of the liquid component storage container.

9. The liquid component collecting device according to claim 1, wherein the first cap further comprises a first protruding part, to which a first tube is connected, arranged on an upper face portion of the first cap on which the liquid component inlet channel is formed, and a second protruding part, to which a second tube is connected, arranged on an upper face portion of the first cap on which the first communication channel is formed.

* * * * *